(12) United States Patent
Manley et al.

(10) Patent No.: US 8,415,363 B2
(45) Date of Patent: Apr. 9, 2013

(54) CRYSTALLINE FORMS OF 4-METHYL-N-[3-(4-METHYL-IMIDAZOL-1-YL)-5-TRIFLUOROMETHYL-PHENYL]-3-(4-PYRIDIN-3-YL-PYRIMIDIN-2-YLAMINO)-BENZAMIDE

(75) Inventors: Paul W Manley, Arlesheim (CH); Wen-Chung Shieh, Berkeley Heights, NJ (US); Paul Allen Sutton, Parsippany, NJ (US); Piotr "Peter" H Karpinski, Lincoln Park, NJ (US); Raeann R Wu, Pine Brook, NJ (US); Stéphanie M Monnier, Raedersheim (FR); Jörg Brozio, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/565,913

(22) Filed: Aug. 3, 2012

(65) Prior Publication Data
US 2013/0023548 A1   Jan. 24, 2013

Related U.S. Application Data

(62) Division of application No. 11/995,906, filed as application No. PCT/US2006/027875 on Jul. 18, 2006, now Pat. No. 8,343,984.

(60) Provisional application No. 60/701,405, filed on Jul. 20, 2005, provisional application No. 60/716,214, filed on Sep. 12, 2005.

(51) Int. Cl.
*A01N 43/54* (2006.01)
*A61K 31/505* (2006.01)
*C07D 239/02* (2006.01)

(52) U.S. Cl.
USPC .......................................... 514/269; 544/316

(58) Field of Classification Search .................. 514/269; 544/316
See application file for complete search history.

(56) References Cited

FOREIGN PATENT DOCUMENTS

| WO | WO 2004/005281 | 1/2004 |
| WO | WO 2005/039586 | 5/2005 |
| WO | WO 2007/015871 | 2/2007 |

OTHER PUBLICATIONS

Berge et al., "Pharmaceutical Salts", Journal of Pharmaceutical sciences, vol. 66. No. 1 pp. 1-19, (1977).
Byrn et al. "Pharmaceutical Solids: A Strategic Approachto Regulatory Considerations", Pharmaceutical Research, vol. 12, No. 7. pp. 945-954, (1995).
Weisberg et al., "Characterization of AMN107, a selective inhibitor of native and mutant Bcr-Abl," Cancer Cell, vol. 7, No. 2, pp. 129-141 (2005).
Grant, DJW, Chapter 1 of "Polymorphism in Pharmaceutical Solids", edited by H.G. Brittain, Marcel Dekker publisher, pp. 1-10 (1999).
Guillory, JK, Chapter 5 of "Polymorphism in Pharmaceutical Solids", e3dited by H.G. Brittain, Marcel Dekker publisher, pp. 183-226 (1999).
Jain, et al., "Polymorphism in Pharmacy", Indian Drugs, vol. 23, No. 6, p. 315-329 (1986).
Carla, Mino R., "Crystalline Polymorphism of Organic Compounds", Topics in Current Chemistry, vol. 198, pp. 163-208 (1998).
Vippagunta, et al, "Crystalline Solids", Advanced Drug Delivery Reviews, vol. 48, No. 1, pp. 3-26 (2001).

*Primary Examiner* — Paul V. Ward
(74) *Attorney, Agent, or Firm* — Stephen Johnson

(57) ABSTRACT

Crystalline forms of 4-methyl-N-[3-(4-methyl-imidazol-1-yl)-5-trifluoromethyl-phenyl]-3-(4-pyridin-3-yl-pyrimidin-2-ylamino)-benzamide free base and salts thereof are prepared by various processes.

8 Claims, 25 Drawing Sheets

CRYSTALLINE FORMS OF 4-METHYL-N-[3-(4-METHYL-IMIDAZOL-1-YL)-5-TRIFLUOROMETHYL-PHENYL]-3-(4-PYRIDIN-3-YL-PYRIMIDIN-2-YLAMINO)-BENZAMIDE

This application is a division of U.S. patent application Ser. No. 11/995,906, which is a National Phase Entry (371) of PCT/US06/27875, filed on Jul. 18, 2006, which claims the benefit of U.S. Provisional Patent Application No. 60/701,405, filed Jul. 20, 2005 and U.S. Provisional Patent Application No. 60/716,214, filed Sep. 12, 2005, the contents of which are hereby incorporated by reference herein in their entirety.

BACKGROUND OF THE INVENTION

1. Field of the Invention

This invention relates to crystalline forms or polymorphs of 4-methyl-N-[3-(4-methyl-imidazol-1-yl)-5-trifluoromethyl-phenyl]-3-(4-pyridin-3-yl-pyrimidin-2-ylamino)-benzamide, as well as to methods of making the same, pharmaceutical compositions comprising the same and methods of treatment using the same.

2. Related Background Art

Polymorphism denotes the existence of more than one crystal structure of a substance. This ability of a chemical substance to crystallize in more than one crystal modification can have a profound effect on the shelf life, solubility, formulation properties, and processing properties of a drug. In addition, the action of a drug can be affected by the polymorphism of the drug molecule. Different polymorphs can have different rates of uptake in the body, leading to lower or higher biological activity than desired. In extreme cases, an undesired polymorph can even show toxicity. The occurrence of an unknown polymorphic form during manufacture can have an enormous impact.

Understanding and controlling polymorphism, then, gives a decided advantage in bringing new drugs to the marketplace. First and foremost, predicting any possible polymorphs for a drug product can be used to diminish the possibility of contamination during a drug's manufacture or storage by other polymorphic forms. Failure to catch contamination can have life-threatening consequences in some cases. Crystallizing an unintended polymorph during manufacture can mean weeks or even months of production downtime while scientists find and correct the cause of the new crystal form or go through another round of testing to obtain approval for the new form.

Second, understanding which crystal structures are possible in some cases allows researchers to maximize the desired properties of a compound, such as solubility, formulation properties, processing properties, and shelf life. Understanding these factors early in the development of a new drug may mean a more active, more stable, or more cheaply manufactured drug.

The compound 4-methyl-N-[3-(4-methyl-imidazol-1-yl)-5-trifluoromethyl-phenyl]-3-(4-pyridin-3-yl-pyrimidin-2-ylamino)-benzamide of the formula

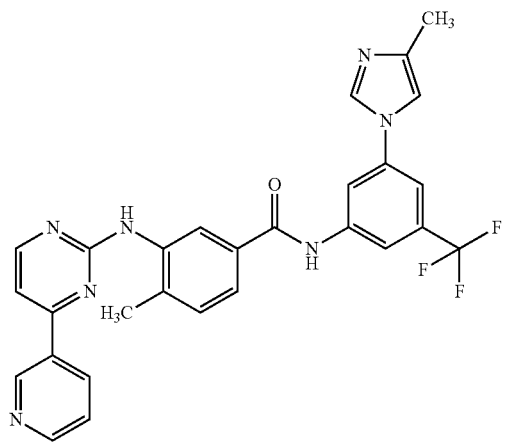 [SMILES: Cc1cn(-c2cc(NC(=O)c3ccc(C)c(Nc4nccc(-c5cccnc5)n4)c3)cc(C(F)(F)F)c2)cn1]

is described in WO 2004/005281 A1, for example, in Example 92. Valuable pharmacological properties are attributed to this compound; thus, it can be used, for example, as a protein kinase inhibitor useful in therapy for diseases which respond to inhibition of protein kinase activity. Knowledge of the potential polymorphic forms of 4-methyl-N-[3-(4-methyl-imidazol-1-yl)-5-trifluoromethyl-phenyl]-3-(4-pyridin-3-yl-pyrimidin-2-ylamino)-benzamide is useful in the development of a suitable dosage form, because the failure to utilize a single polymorphic form during clinical or stability studies may result in the exact dosage form being used or studied not being comparable from one lot to another. Once chosen, it is important that a polymorphic form can be reproducibly prepared and remain unchanged for prolonged time periods in the dosage form developed. It is also desirable to have a process for producing 4-methyl-N-[3-(4-methyl-imidazol-1-yl)-5-trifluoromethyl-phenyl]-3-(4-pyridin-3-yl-pyrimidin-2-ylamino)-benzamide in high purity since the presence of impurities may produce undesired toxicological effects.

WO 2004/005281 A1 provides no information at all about possible crystal modifications of 4-methyl-N-[3-(4-methyl-imidazol-1-yl)-5-trifluoromethyl-phenyl]-3-(4-pyridin-3-yl-pyrimidin-2-ylamino)-benzamide. The compound is recrystallized from a mixture of tetrahydrofuran and ethyl acetate, but WO 2004/005281 A1 gives no indication that the particular recrystallization used therein is to be applied or that particular conditions might be adopted to modify the crystalline form achieved. It has now surprisingly been found that the different crystal modifications (novel polymorphic forms of 4-methyl-N-[3-(4-methyl-imidazol-1-yl)-5-trifluoromethyl-phenyl]-3-(4-pyridin-3-yl-pyrimidin-2-ylamino)-benzamide) characterized below can be prepared by choice of specially selected process conditions, e.g., choice of solvent system, duration of crystallization, etc.

SUMMARY OF THE INVENTION

The present invention is directed to substantially pure crystalline forms of 4-methyl-N-[3-(4-methyl-imidazol-1-yl)-5-trifluoromethyl-phenyl]-3-(4-pyridin-3-yl-pyrimidin-2-ylamino)-benzamide free base.

The present invention is also directed to substantially pure crystalline forms of the hydrochloride and sulfate salts of 4-methyl-N-[3-(4-methyl-imidazol-1-yl)-5-trifluoromethyl-phenyl]-3-(4-pyridin-3-yl-pyrimidin-2-ylamino)-benzamide.

The invention is further directed to pharmaceutical compositions comprising:
(a) a therapeutically effective amount of a substantially pure crystalline form of 4-methyl-N-[3-(4-methyl-imidazol-1-yl)-5-trifluoromethyl-phenyl]-3-(4-pyridin-3-yl-pyrimidin-2-ylamino)-benzamide free base or salt thereof of the present invention; and
(b) at least one pharmaceutically acceptable carrier, diluent, vehicle or excipient.

The present invention is also directed to a method of treating a disease which responds to an inhibition of protein kinase activity comprising the step of administering to a subject in need of such treatment a therapeutically effective amount of a substantially pure crystalline form of 4-methyl-N-[3-(4-methyl-imidazol-1-yl)-5-trifluoromethyl-phenyl]-3-(4-pyridin-3-yl-pyrimidin-2-ylamino)-benzamide free base or salt thereof of the present invention.

Figure 1:
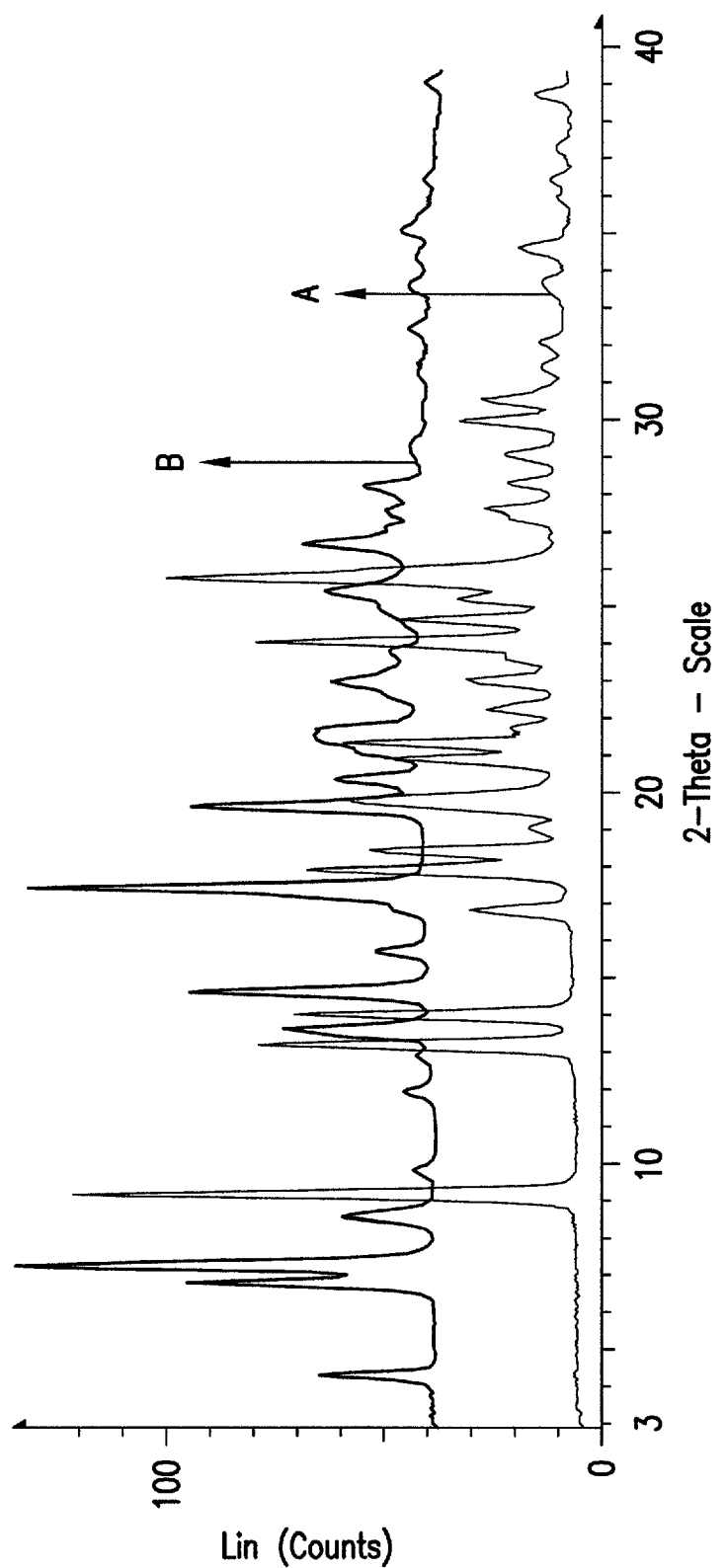
FIG. 1 shows the x-ray powder diffraction patterns (XR-PDs) for forms A and B of 4-methyl-N-[3-(4-methyl-imidazol-1-yl)-5-trifluoromethyl-phenyl]-3-(4-pyridin-3-yl-pyrimidin-2-ylamino)-benzamide free base according to the present invention.
Figure 2:
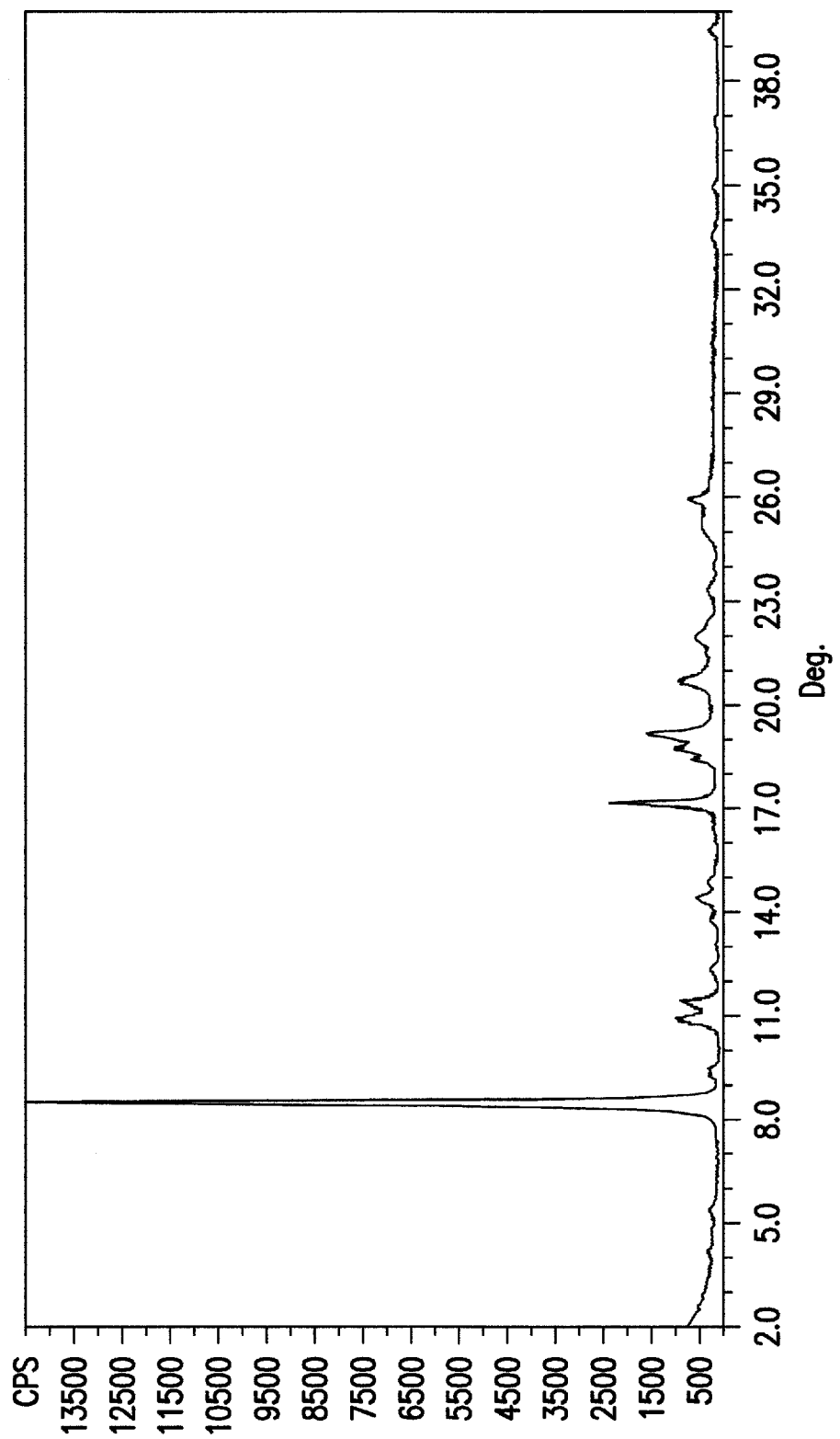
FIG. 2 shows the x-ray powder diffraction pattern (XRPD) for form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.

DETAILED DESCRIPTION OF THE INVENTION 4-methyl-N-[3-(4-methyl-imidazol-1-yl)-5-trifluoromethyl-phenyl]-3-(4-pyridin-3-yl-pyrimidin-2-ylamino)-benzamide free base, 4-methyl-N-[3-(4-methyl-imidazol-1-yl)-5-trifluoromethyl-phenyl]-3-(4-pyridin-3-yl-pyrimidin-2-ylamino)-benzamide hydrochloride and 4-methyl-N-[3-(4-methyl-imidazol-1-yl-5-trifluoromethyl-phenyl]-3-(4-pyridin-3-yl-pyrimidin-2-ylamino)-benzamide sulfate can be obtained in various crystalline forms. These "crystalline form(s)" (or "crystalline modification(s)" or "polymorphic form(s)" or "polymorph(s)", as the terms will be used interchangeably herein) differ with respect to thermodynamic stability, physical parameters, x-ray structure and preparation processes. While polymorphism classically refers to the ability of a compound to crystallize into more than one distinct crystal species (having identical chemical structure but quite different physicochemical properties), the term pseudopolymorphism is typically applied to solvate and hydrate crystalline forms. For purposes of this invention, however, both true polymorphs as well as pseudopolymorphs, i.e., hydrate and solvate forms, are included in the scope of "crystalline forms". In addition, "amorphous" refers to a disordered solid state. It should be noted that different samples of a particular crystalline form will share the same major XRPD peaks, but that there can be variation in powder patterns with regard to minor peaks. In addition, the term "about" with regard to XRPD maxima values (in °) generally means within 0.3°, more preferably within 0.2°, and most preferably within 0.1° of the given value; alternatively, the term "about" means (in this and all contexts) within an accepted standard of error of the mean, when considered by one of ordinary skill in the art. As used herein, the terms "isolated" and/or "substantially pure" mean more than 50% of the crystalline 4-methyl-N-[3-(4-methyl-imidazol-1-yl)-5-trifluoromethyl-phenyl]-3-(4-pyridin-3-yl-pyrimidin-2-ylamino)-benzamide or salt thereof is present in one of the forms described herein and preferably at least 70%, more preferably at least 80%, and most preferably at least 90% of one of the crystalline forms described herein is present.

The first embodiment of the present invention is directed to a substantially pure crystalline form A of 4-methyl-N-[3-(4-methyl-imidazol-1-yl)-5-trifluoromethyl-phenyl]-3-(4-pyridin-3-yl-pyrimidin-2-ylamino)-benzamide free base. Form A of the free base is slightly hygroscopic (maximum water uptake of less than 2% at 25° C. up to 80% r.h.) and has rather low solubility in an aqueous buffer solution, i.e., 2 mg/L at pH 6.8 and >200 mg/L at pH 1.0; hygroscopic behavior is reversible. Form A's basic thermal properties were studied by thermogravimetric analysis (TGA) and differential scanning calorimetry (DSC) and are as follows:

TABLE 1

Thermal Properties of Free Base form A

| | |
|---|---|
| Melting point (onset) | ~232° C. |
| Decomposition temperature | >300° C. |
| Loss on drying | <0.10% (RT-200° C.) |

The x-ray powder diffraction pattern of free base form A shows at least one, more preferably at least two, still more preferably at least four, and most preferably all, maxima selected from about 9.2°, 13.1°, 13.9°, 16.7°, 17.9°, 18.4°, 19.8°, 24.1° and 25.8° (2θ degrees). The term "about" applies to each listed maxima for this and all other forms addressed in this invention. A particularly preferred embodiment of the present invention is directed to a substantially pure crystalline form A of 4-methyl-N-[3-(4-methyl-imidazol-1-yl)-5-trifluoromethyl-phenyl]-3-(4-pyridin-3-yl-pyrimidin-2-ylamino)-benzamide free base as characterized by the XRPD of FIG. 1.

The second embodiment of the present invention is directed to a substantially pure crystalline form B of 4-methyl-N-[3-(4-methyl-imidazol-1-yl)-5-trifluoromethyl-phenyl]-3-(4-pyridin-3-yl-pyrimidin-2-ylamino)-benzamide free base. Form B of the free base is not hygroscopic (maximum water uptake of less than 0.2% at 25° C. up to 80% r.h.) and has rather low solubility in an aqueous buffer solution, i.e., 0.2 mg/L at pH 6.8, 2.8 mg/L at pH 2.8 and 839 mg/L at pH 1.0; hygroscopic behavior is reversible. Form B's basic thermal properties were studied by thermogravimetric analysis and differential scanning calorimetry and are as follows:

TABLE 2

Thermal Properties of Free Base form B

| | |
|---|---|
| Melting point (onset) | ~245° C. |
| Decomposition temperature | >300° C. |
| Loss on drying | <0.12% (RT-200° C.) |

The x-ray powder diffraction pattern of free base form B shows at least one, more preferably at least two, still more preferably at least four, and most preferably all, maxima selected from about 4.3°, 6.8°, 7.2°, 13.5°, 14.5°, 17.4°, 19.6° and 26.7° (2θ degrees). A particularly preferred embodiment of the present invention is directed to a substantially pure crystalline form B of 4-methyl-N-[3-(4-methyl-imidazol-1-yl)-5-trifluoromethyl-phenyl]-3-(4-pyridin-3-yl-pyrimidin-2-ylamino)-benzamide free base as characterized by the XRPD of FIG. 1.

Figure 25:
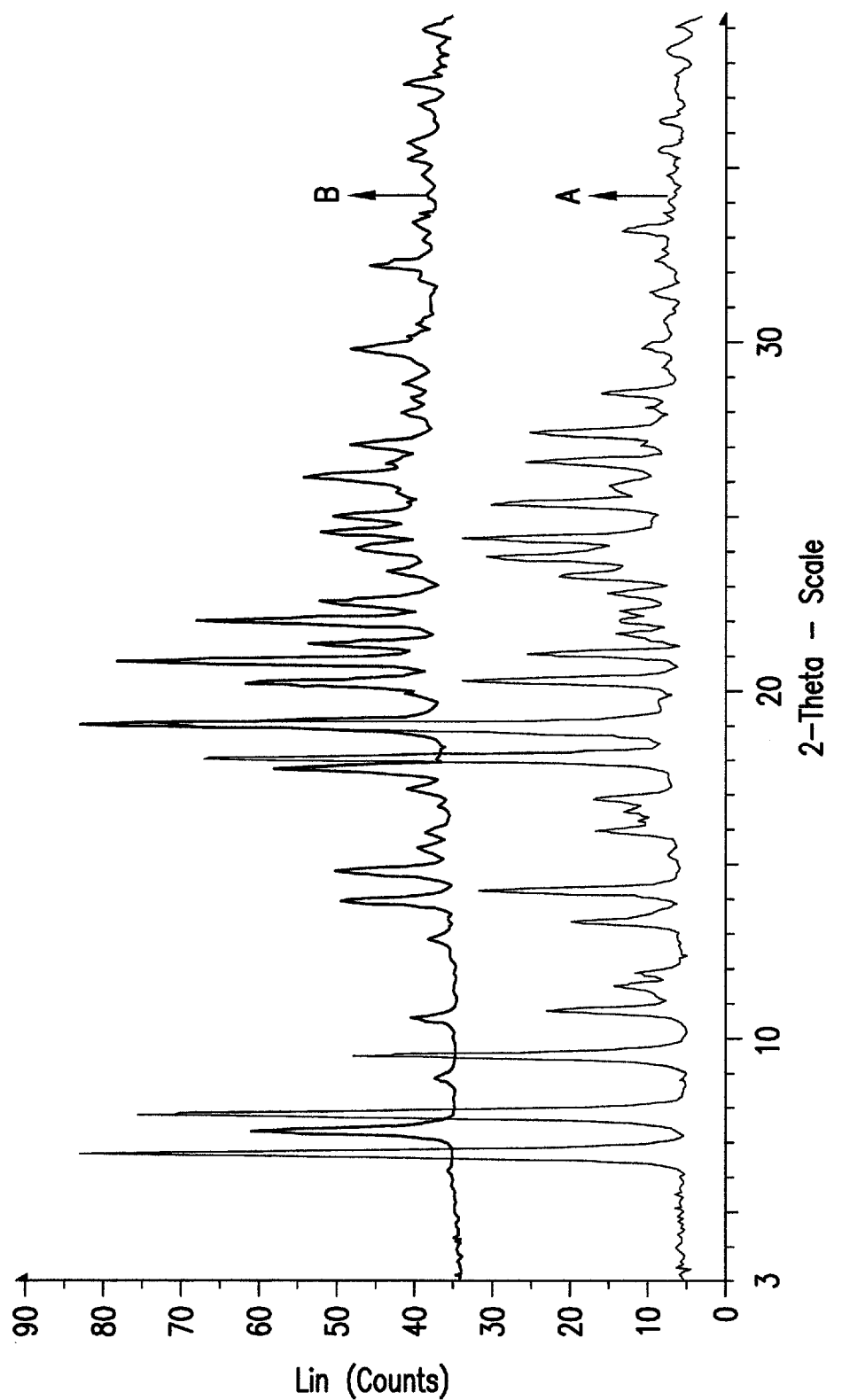
FIG. 25 shows the x-ray powder diffraction patterns for forms A and B of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.

In addition, various isolated salt forms of 4-methyl-N-[3-(4-methyl-imidazol-1-yl)-5-trifluoromethyl-phenyl]-3-(4-pyridin-3-yl-pyrimidin-2-ylamino)-benzamide also have been shown to exhibit polymorphism, i.e., will tend to crystallize under various crystalline forms. For example, each of the hydrochloride and sulfate salts exhibits several distinct crystalline forms. As used herein, "salt" refers to a compound prepared by the reaction of an organic acid or base drug with a pharmaceutically acceptable mineral or organic acid or base; suitable pharmaceutically acceptable minerals or organic acids or bases are as listed in Tables 1-8 in *Handbook of Pharmaceutical Salts*, P. H. Stahl and C. G. Wermuth (eds.), VHCA, Zurich, pp. 334-345 (2002). Co-pending U.S. Patent Application No. 60/701,406, filed concurrently herewith, addresses salts and the methods by which salts of 4-methyl-N-[3-(4-methyl-imidazol-1-yl)-5-trifluoromethyl-phenyl]-3-(4-pyridin-3-yl-pyrimidin-2-ylamino)-benzamide may be made, respectively. The disclosure of that application is incorporated in its entirety by reference herein. Forms A, A', A", B, B', $S_B$, $S_{B'}$, C, C', $S_C$, D and $S_E$ for the hydrochloride salt can be characterized by the XRPD patterns shown in FIGS. 2, 6-8, 12-15 and 18-21, respectively. Forms A and B for the sulfate salt can be characterized by the XRPD patterns shown in FIG. 25. Accordingly, additional embodiments of the present invention are directed to each of these substantially pure crystalline forms of the noted salts of 4-methyl-N-[3-(4-methyl-imidazol-1-yl)-5-trifluoromethyl-phenyl]-3-(4-pyridin-3-yl-pyrimidin-2-ylamino)-benzamide.

Form A of the hydrochloride salt is a dihydrate which has relatively poor crystallinity. In the presence of methanol vapor, form A converts to form B (described below). A DSC scan of form A indicates that the dehydration of form A (typically above 77° C.) is complex; a final endothermic event at about 210° C. corresponds to melting as shown by DSC, TGA and XRPD. XRPD at various temperatures shows an intermediate form between about 105-135° C. (Form A' described further below), which is the corresponding monohydrate form, and an anhydrous form (Form A" described further below) was obtained from about 135° C. up; after heating up to about 205° C., form A" retains its form upon holding at about 40° C. for about 30 minutes.

Figure 3:
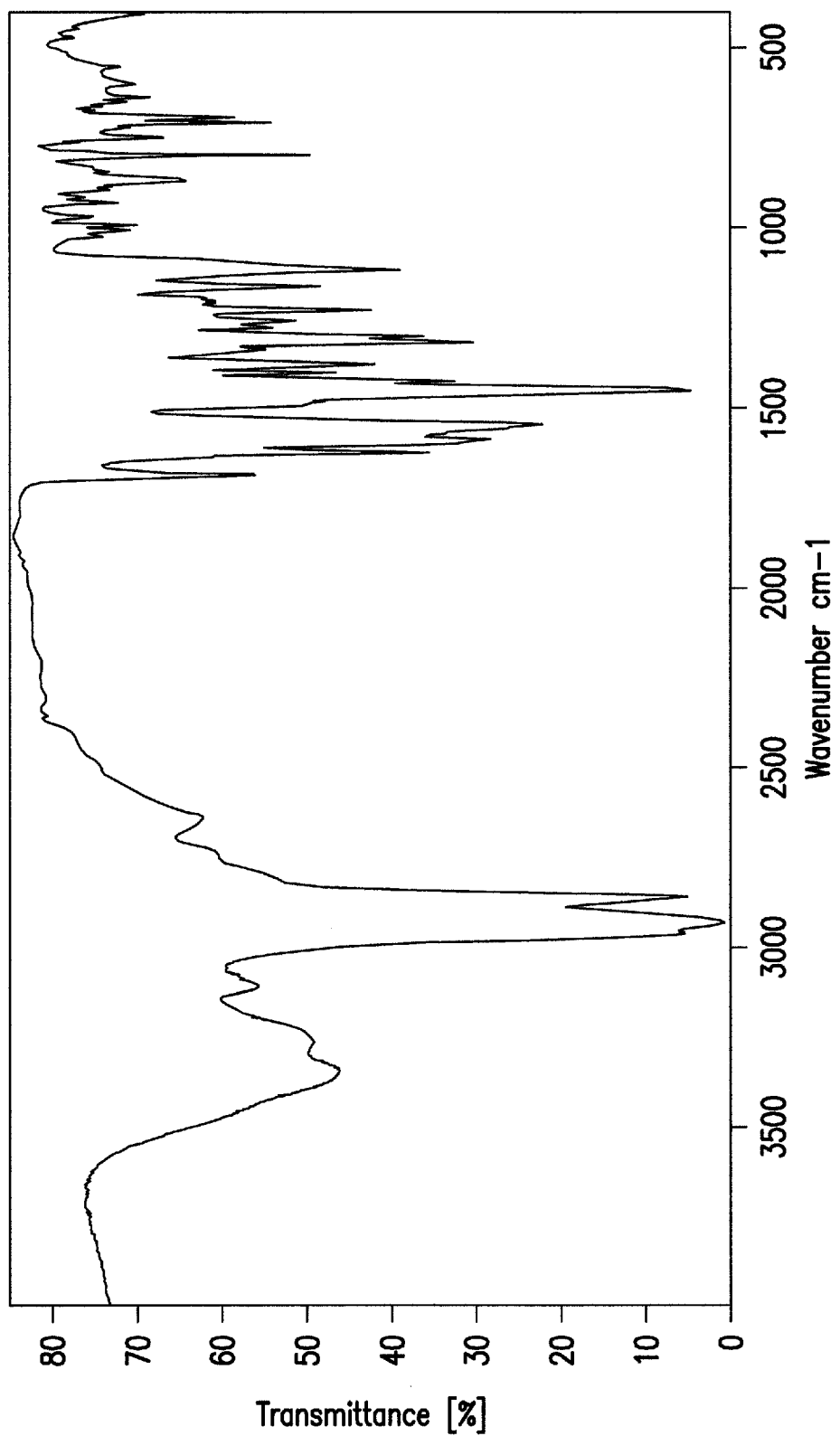
FIG. 3 shows the fourier transform infrared (FT-IR) spectrum for form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as recorded in Nujol mull between two KBr plates using a Bruker IFS-55 instrument.
Figure 4:
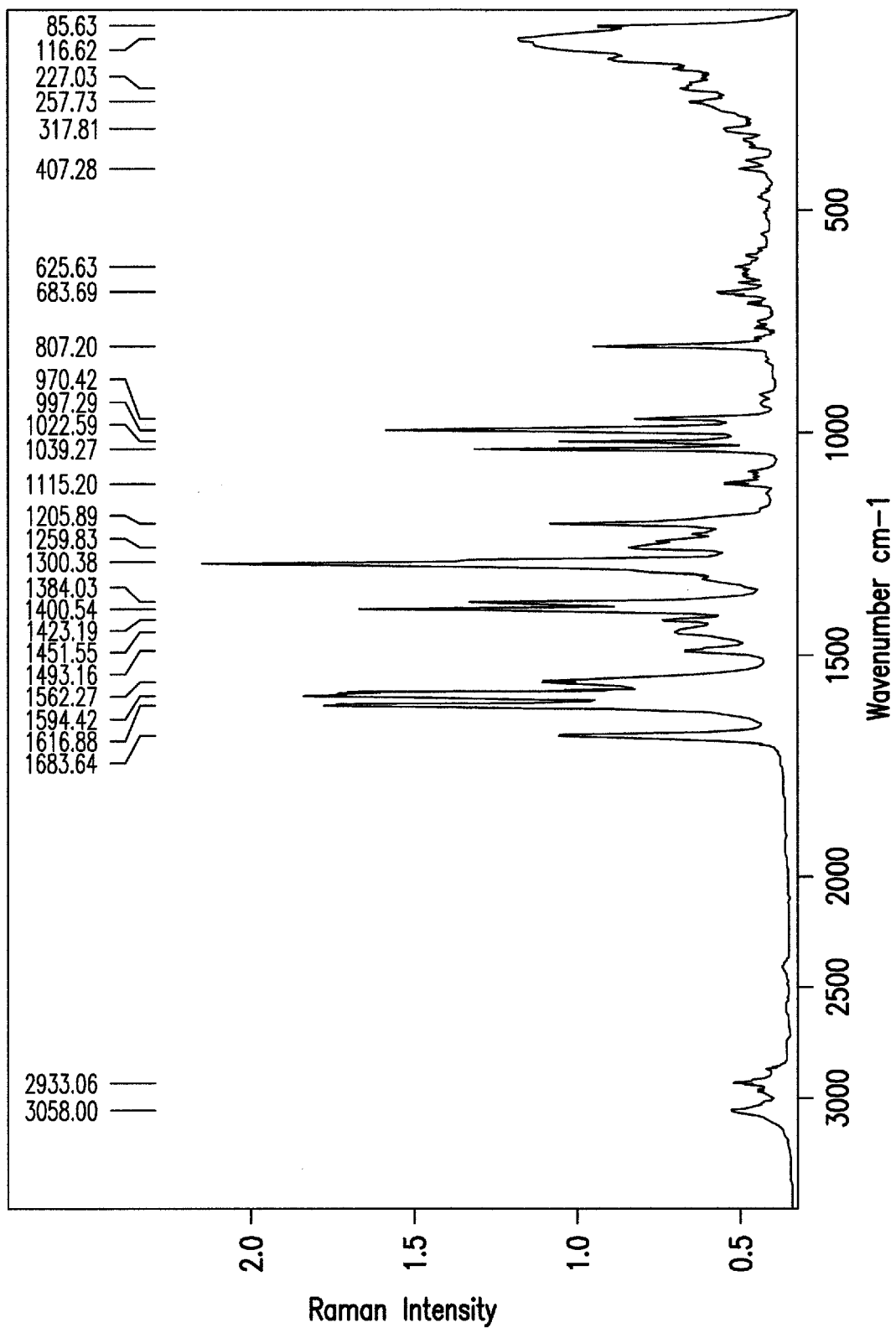
FIG. 4 shows the fourier transform Raman (FT-RAMAN) spectrum for form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as recorded using a Bruker RFS-100 instrument.
Figure 5:
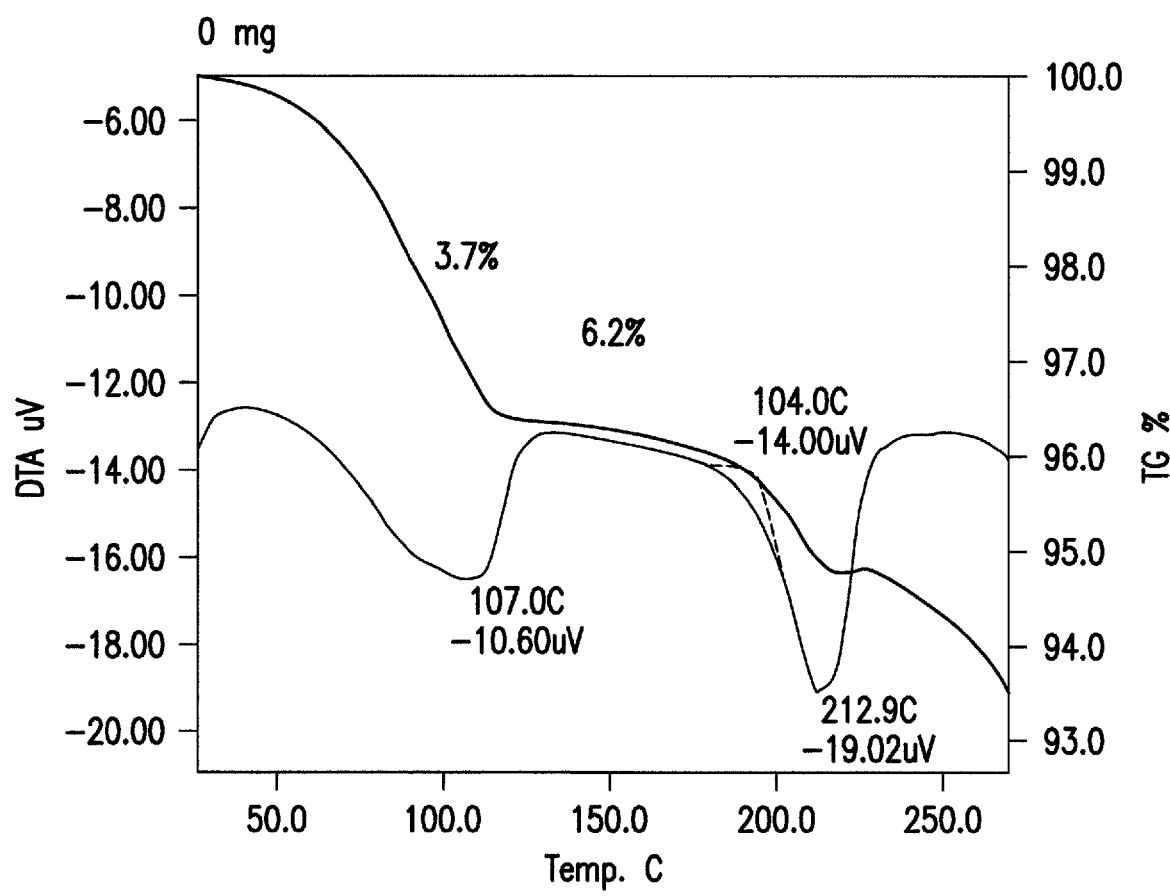
FIG. 5 shows the thermogravimetry and differential thermal analysis curve for form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 6:
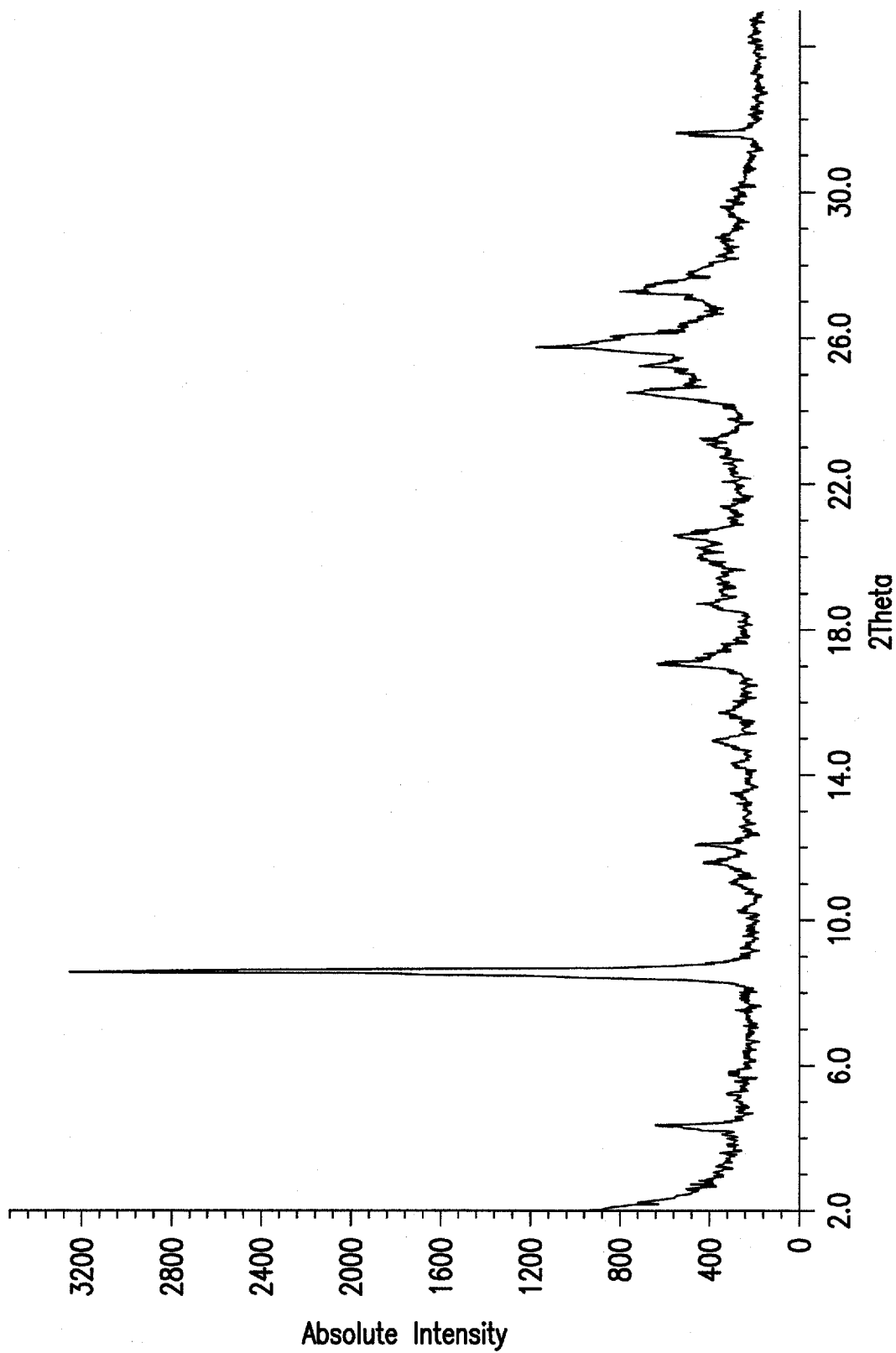
FIG. 6 shows the x-ray powder diffraction pattern for form A' of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 7:
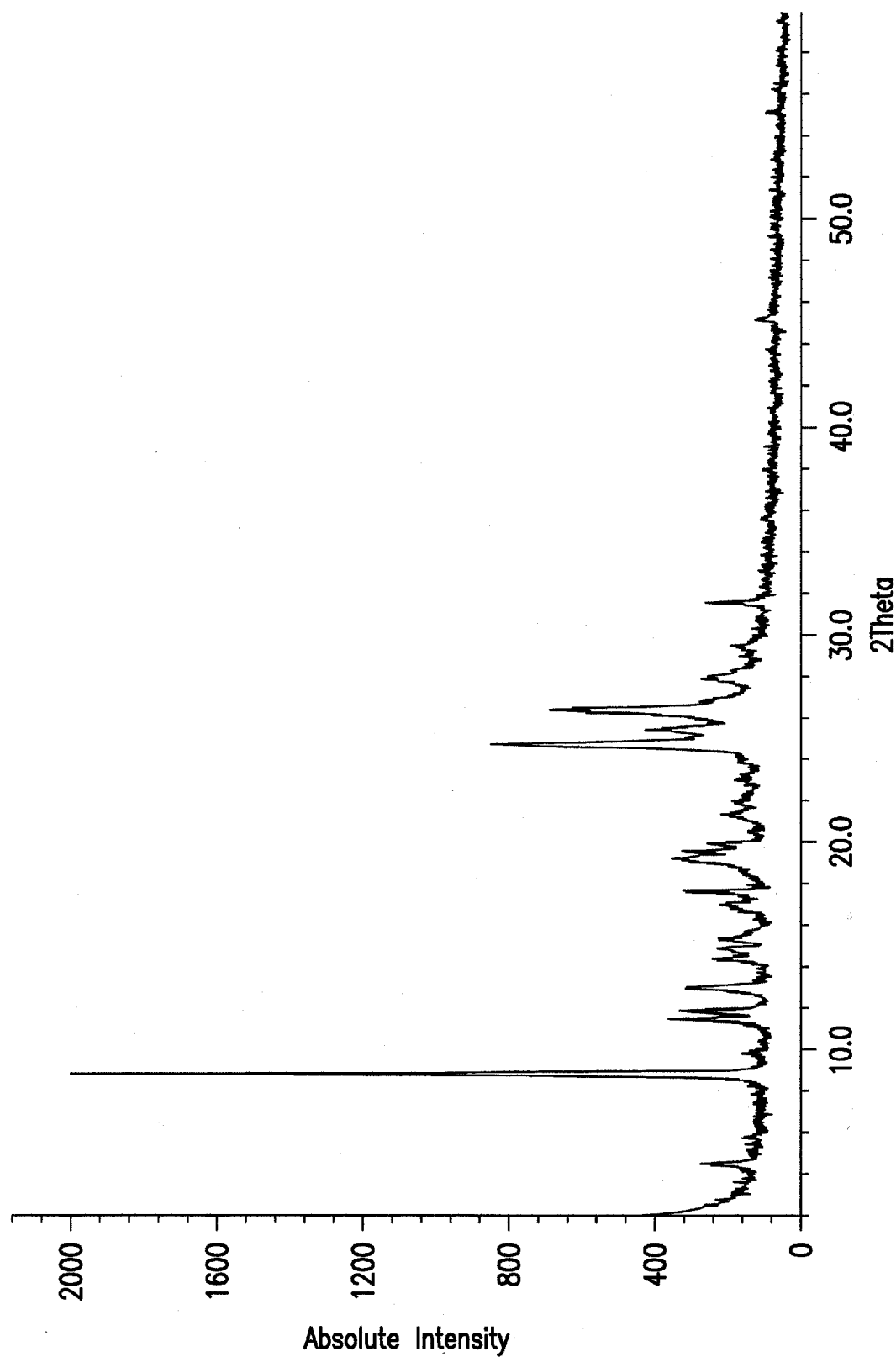
FIG. 7 shows the x-ray powder diffraction pattern for form A" of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.

The x-ray powder diffraction pattern for form A of the hydrochloride salt shows at least one, more preferably at least two, still more preferably at least four, and most preferably all, maxima selected from about 8.5°, 11.0°, 11.5°, 17.2°, 18.8°, 19.2°, 20.8°, 22.1° and 26.0° (2θ degrees). A particularly preferred embodiment of the present invention is directed to a substantially pure crystalline form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 2. The FT-IR spectrum of form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is as shown in FIG. 3. The main IR bands are about: 3342, 2925, 2854, 1682, 1619, 1541, 1448, 1421, 1399, 1378, 1316, 1299, 1255, 1226, 1159, 1147, 1099, 1089, 930, 868, 798, 749, 708, and 693 $cm^{-1}$. In a preferred embodiment of the present invention, a substantially pure crystalline form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is characterized by an FT-IR spectrum having at least one, more preferably at least two, still more preferably at least four, and most preferably all, of the IR bands noted above. The FT-RAMAN spectrum of form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is as shown in FIG. 4. The main RAMAN bands are about: 3059, 2933, 1684, 1617, 1594, 1562, 1493, 1452, 1423, 1401, 1384, 1300, 1260, 1115, 1039, 1023, 997, 970, 807, 684, 627, 407, 318, 258, 227, 117, and 86 $cm^{-1}$. In a preferred embodiment of the present invention, a substantially pure crystalline form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is characterized by an FT-RAMAN spectrum having at least one, more preferably at least two, still more preferably at least four, and most preferably all, of the RAMAN bands noted above. The thermogravimetry and differential thermal analysis (TG-DTA) curve for form A of the hydrochloride salt is shown in FIG. 5.

Additional crystalline forms related to form A of the hydrochloride salt include form A' and form A", which represent a monohydrate of form A and an anhydrous form of form A, respectively. Form A' converts within a few minutes under room conditions to form A. The x-ray powder diffraction pattern for form A' (monohydrate) of the hydrochloride salt shows at least one, more preferably at least two, still more preferably at least four, and most preferably all, maxima selected from about 4.3°, 8.6°, 11.6°, 12.1°, 17.1°, 20.6°, 24.5°, 25.3°, 25.8°, 27.3° and 31.6° (2θ degrees). A particularly preferred embodiment of the present invention is directed to a substantially pure crystalline form A' of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 6. The x-ray powder diffraction pattern for form A" (anhydrous) of the hydrochloride salt shows at least one, more preferably at least two, still more preferably at least four, and most preferably all, maxima selected from about 4.5°, 8.8°, 11.5°, 11.9°, 13.0°, 14.4°, 14.8°, 15.3°, 16.9°, 17.6°, 19.2°, 19.5°, 19.9°, 21.3°, 24.6°, 25.4°, 26.4°, 27.9°, and 31.5° (2θ degrees). A particularly preferred embodiment of the present invention is directed to a substantially pure crystalline form A" of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 7.

Crystalline form B of the hydrochloride salt is a monohydrate which has a theoretical moisture content of 3.1% and shows superior crystallinity and physical stability with respect to form A of the hydrochloride salt. In the presence of ethanol, form B converts to form A. A DSC scan of form B shows a first endotherm at about 100° C.-120° C. which corresponds to dehydration, i.e., transition to an anhydrous crystalline form B'; DSC also shows a second endotherm at about 190° C. which corresponds to melting. XRPD at various temperatures shows anhydrous form B' between about 145° C.-195° C.; after melting at about 195° C., form B' becomes amorphous upon holding at about 40° C. for about 30 minutes. Form B' converts within a few minutes under room conditions to form B.

Figure 8:
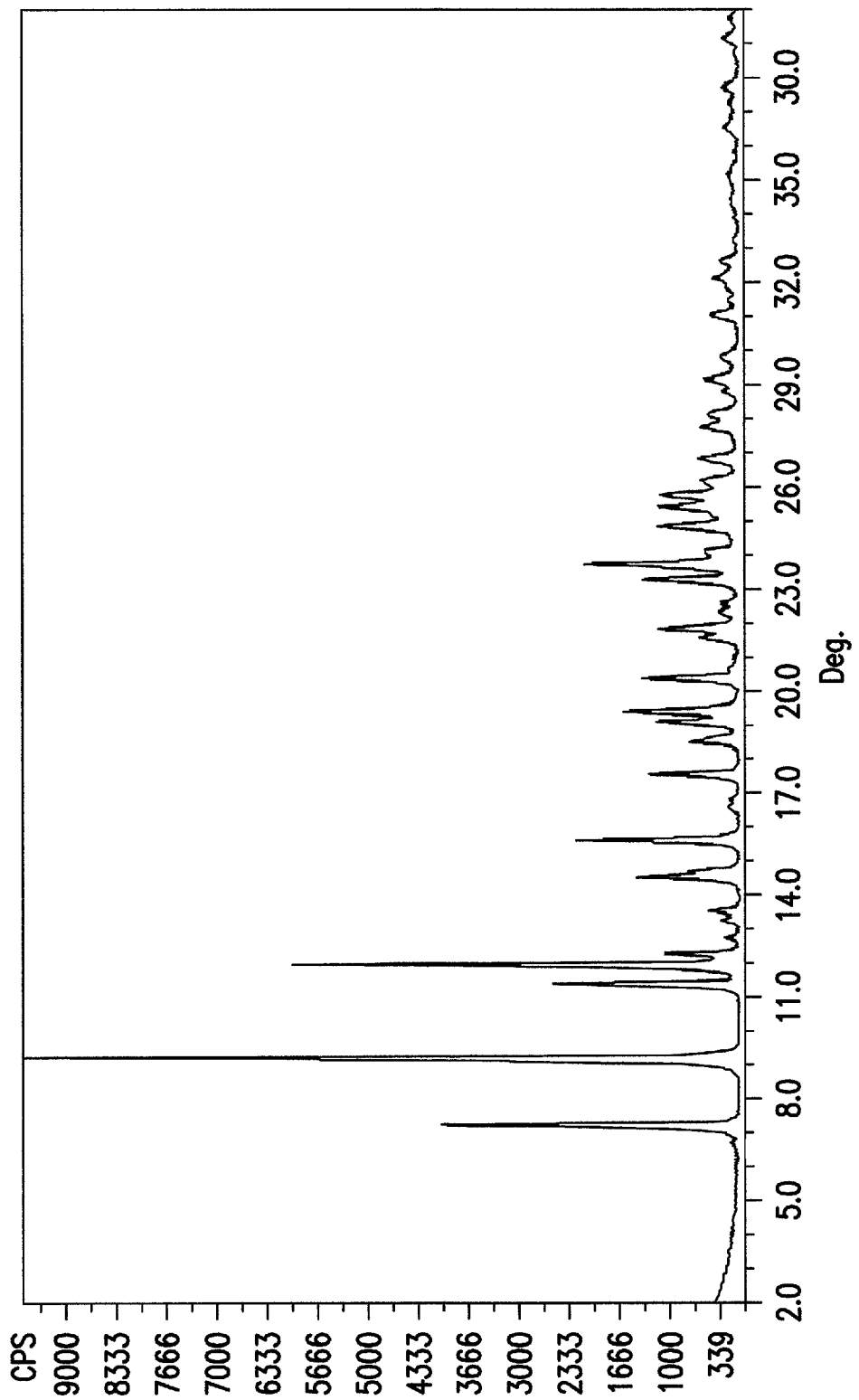
FIG. 8 shows the x-ray powder diffraction pattern for form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 9:
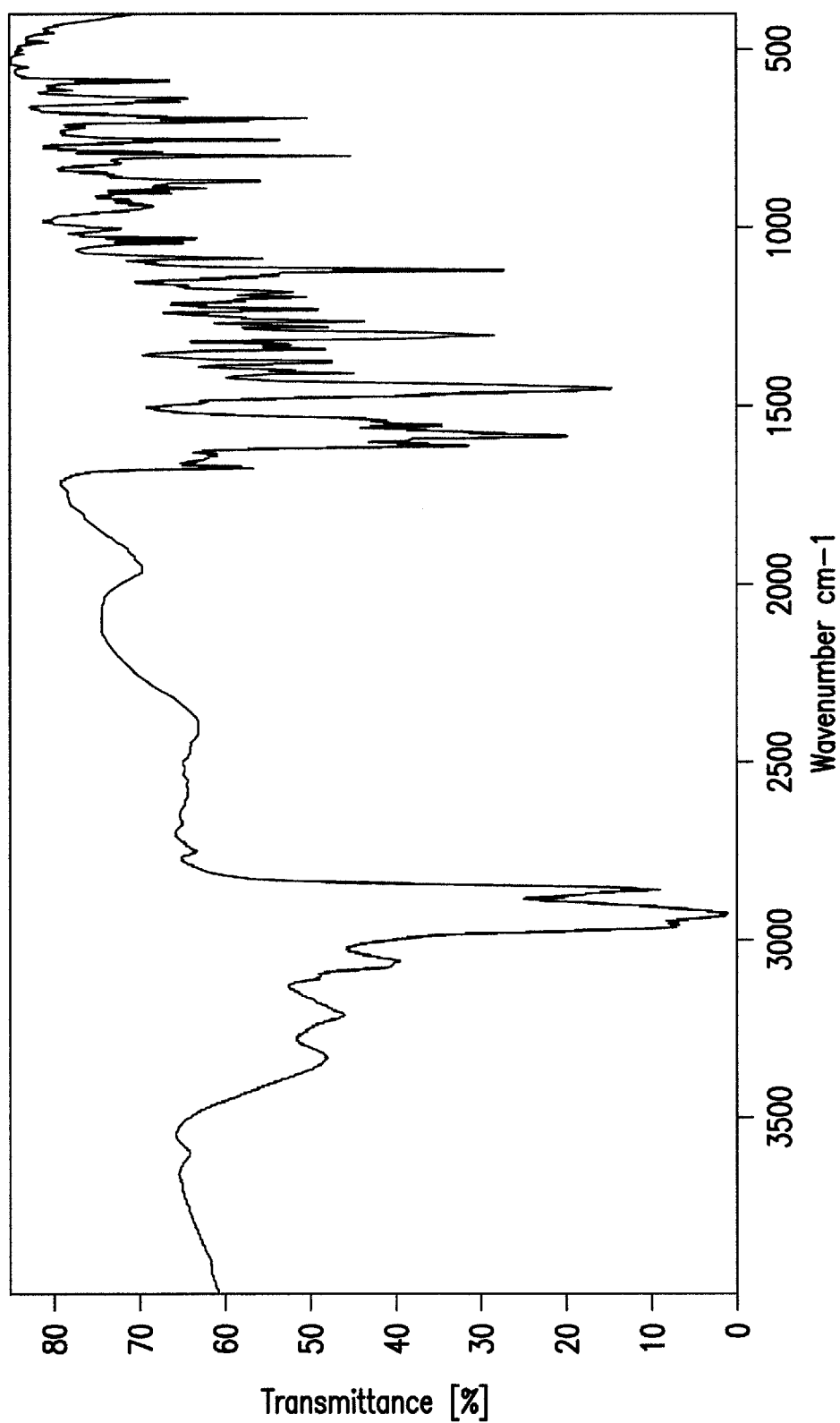
FIG. 9 shows the FT-IR spectrum for form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as recorded in Nujol mull between two KBr plates using a Bruker IFS-55 instrument.
Figure 10:
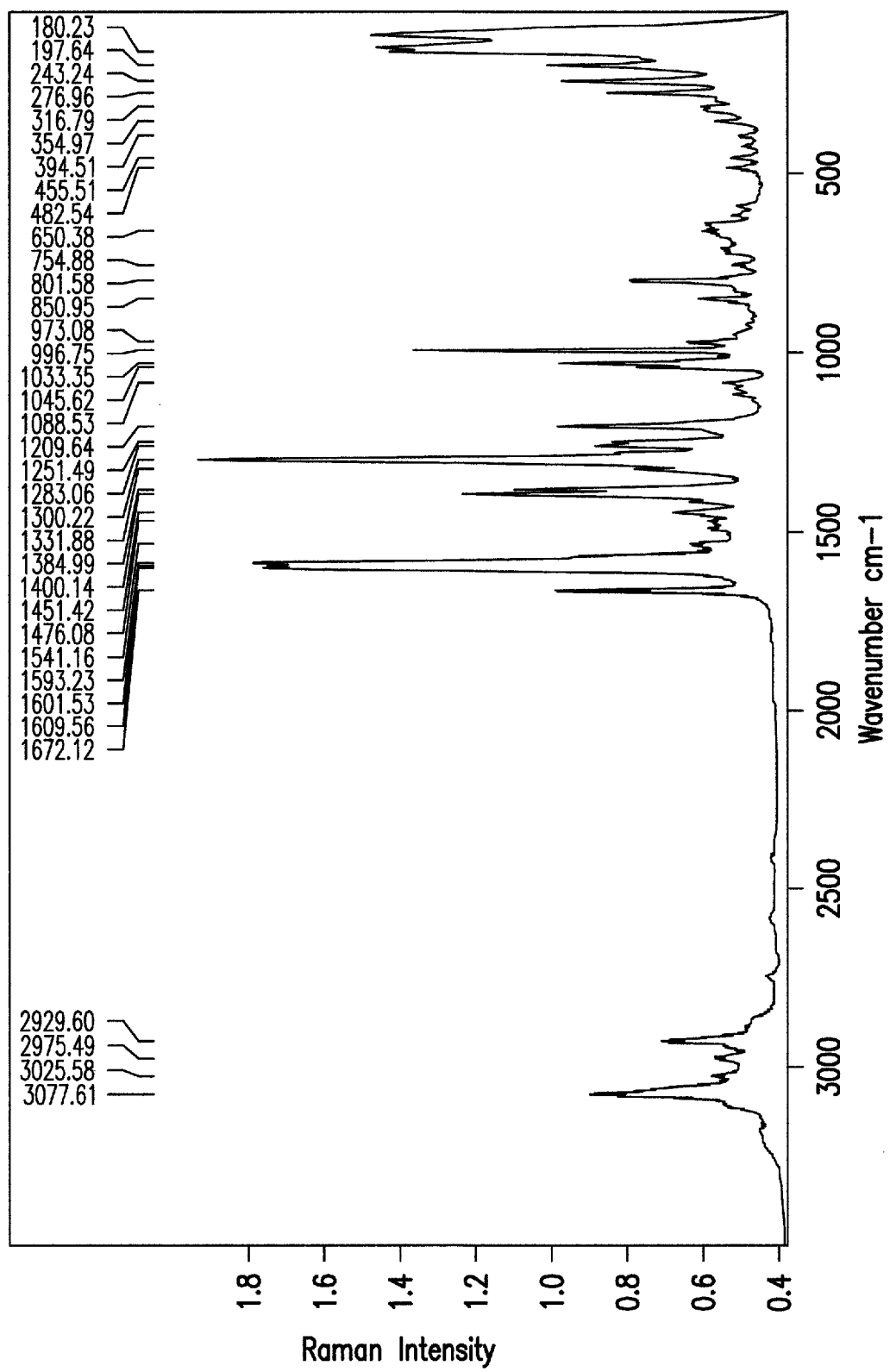
FIG. 10 shows the FT-RAMAN spectrum for form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as recorded using a Bruker RFS-100 instrument.
Figure 11:
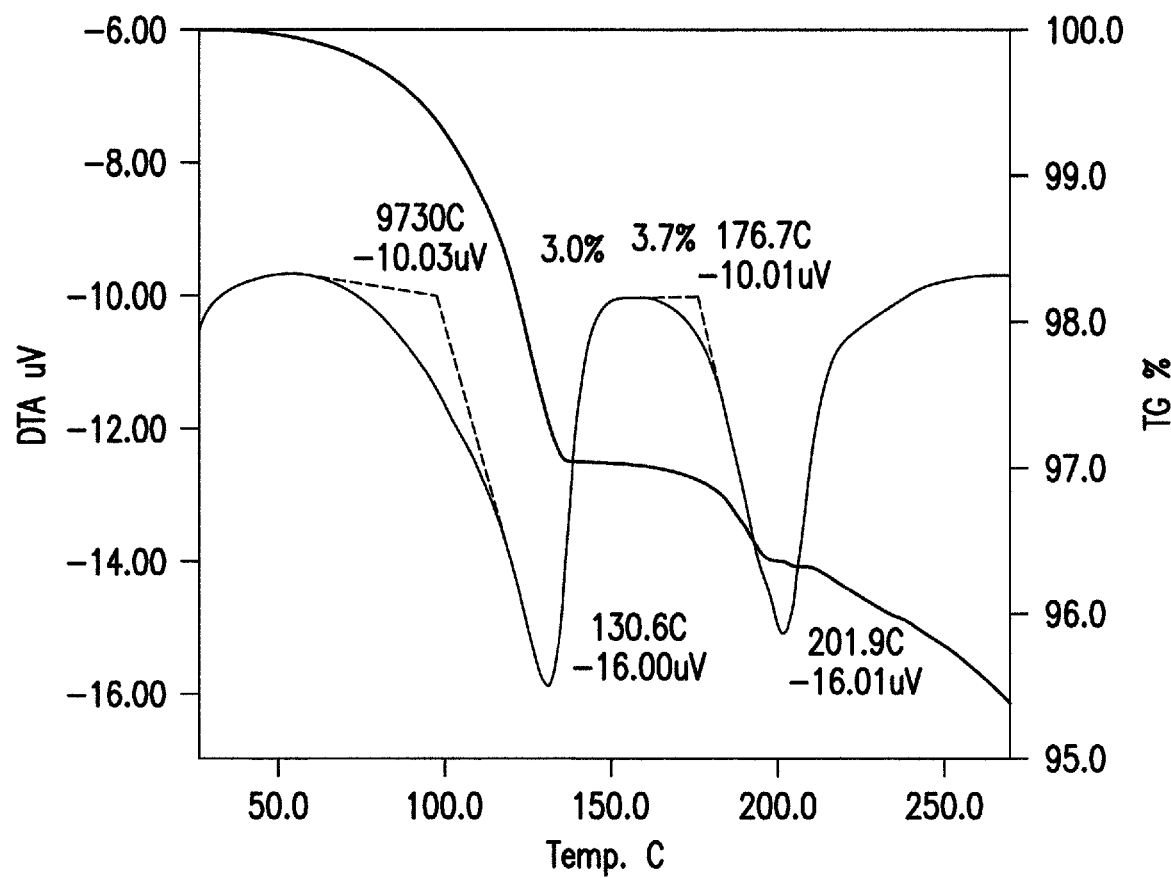
FIG. 11 shows the thermogravimetry and differential thermal analysis curve for form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 12:
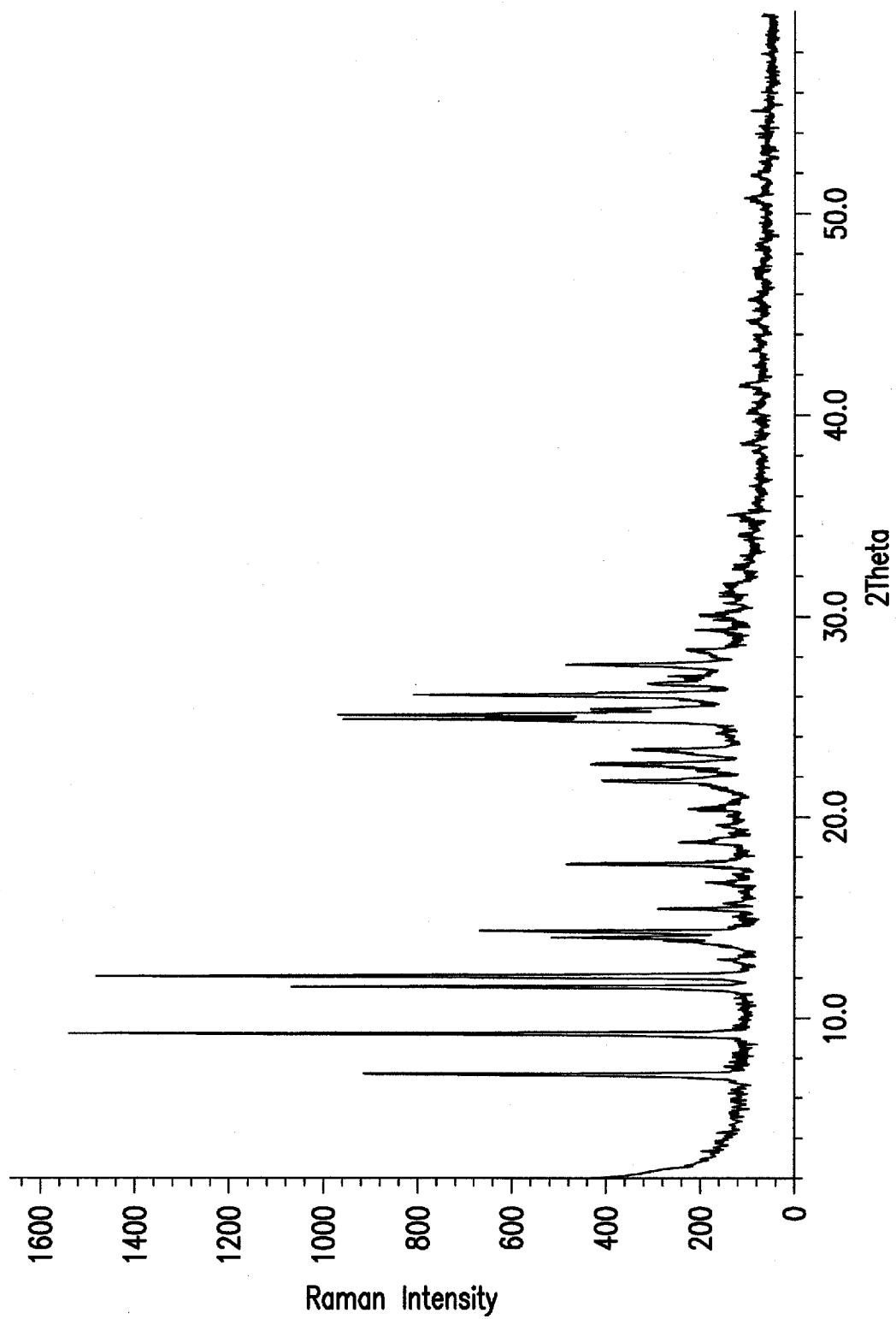
FIG. 12 shows the x-ray powder diffraction pattern for form B' of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 13:
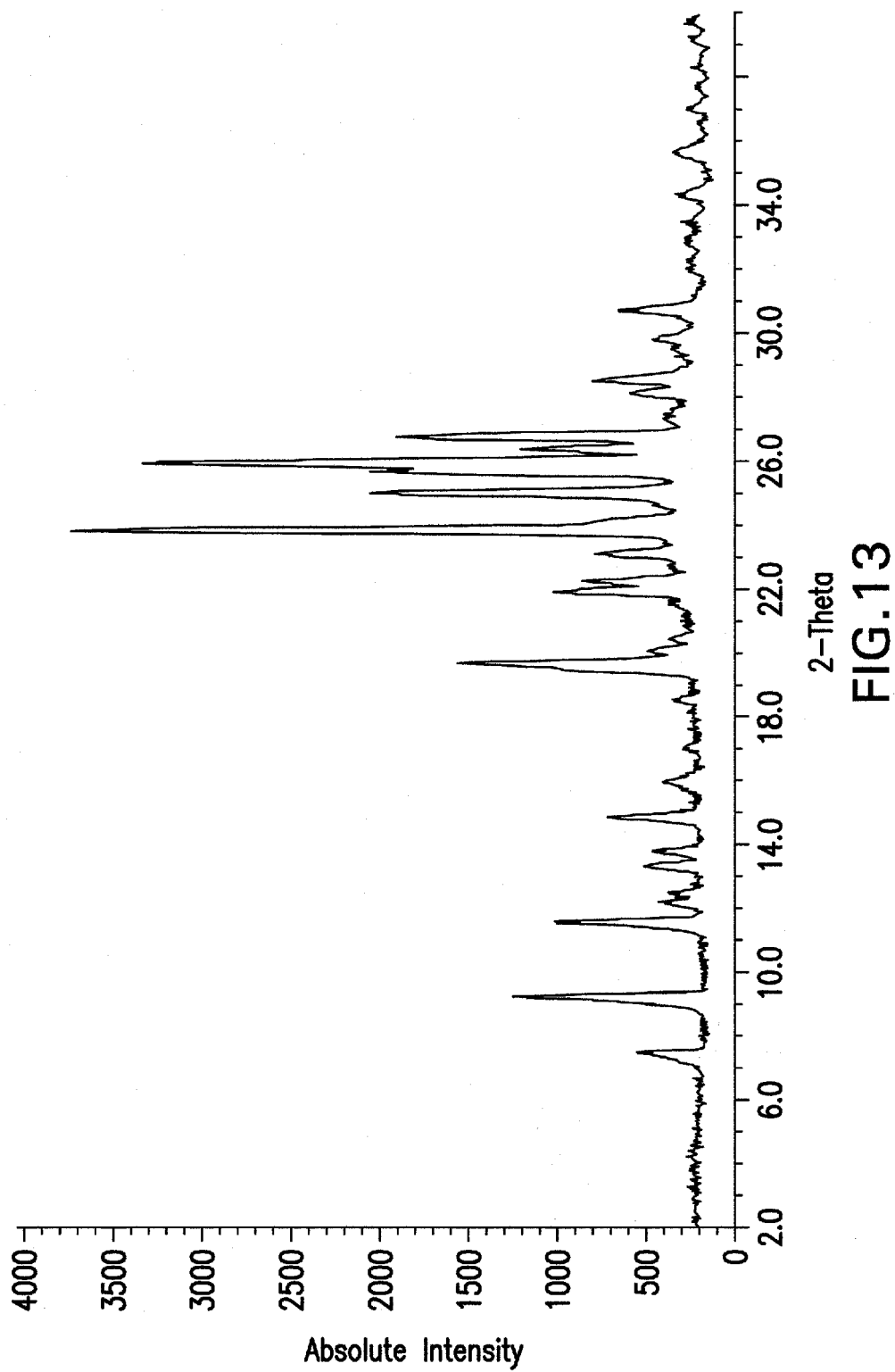
FIG. 13 shows the x-ray powder diffraction pattern for form $S_B$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 14:
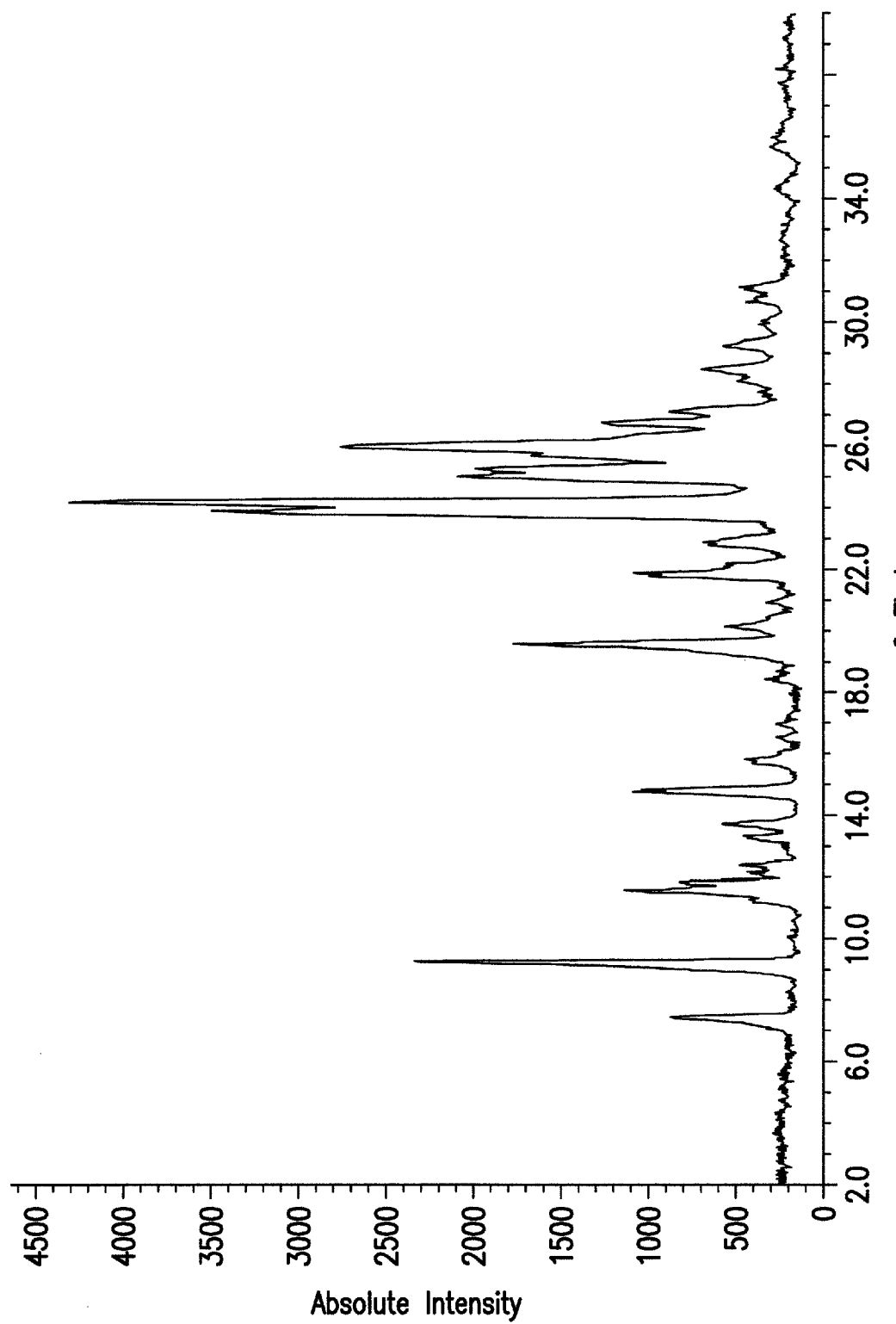
FIG. 14 shows the x-ray powder diffraction pattern for form $S_{B'}$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 15:
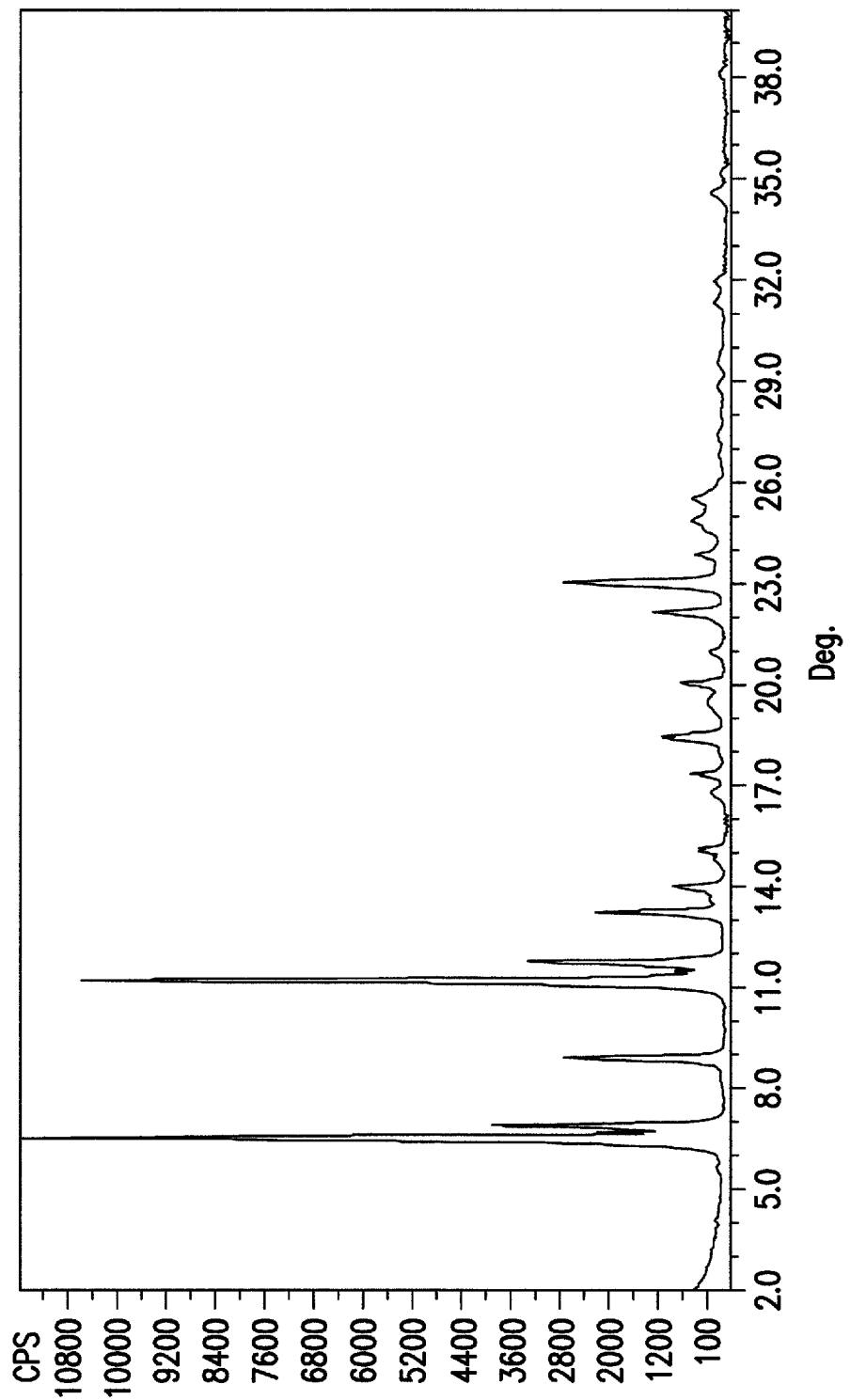
FIG. 15 shows the x-ray powder diffraction pattern for form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.

The x-ray powder diffraction pattern for form B of the hydrochloride salt shows at least one, more preferably at least two, still more preferably at least four, and most preferably all, maxima selected from about 7.2°, 9.2°, 11.4°, 12.0°, 12.3°, 14.6°, 14.8°, 15.7°, 17.6°, 19.2°, 19.5°, 20.5°, 22.0°, 23.4°, 23.9°, 25.0°, 25.5°, 25.9°, 27.0° (2θ degrees). A particularly preferred embodiment of the present invention is directed to a substantially pure crystalline form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 8. The FT-IR spectrum of form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is as shown in FIG. 9. The main IR bands are about: 3211, 3058, 2925, 2854, 1676, 1614, 1587, 1454, 1411, 1378, 1343, 1304, 1279, 1263, 1230, 1197, 1181, 1120, 1089, 1046, 1033, 1005, 905, 892, 874, 801, 755, 706, and 695 $cm^{-1}$. In a preferred embodiment of the present invention, a substantially pure crystalline form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is characterized by an FT-IR spectrum having at least one, more preferably at least two, still more preferably at least four, and most preferably all, of the IR bands noted above. The FT-RAMAN spectrum of form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is as shown in FIG. 10. The main RAMAN bands are about: 3078, 3026, 2975, 2930, 1672, 1610, 1602, 1593, 1541, 1476, 1451, 1400, 1385, 1332, 1303, 1263, 1251, 1210, 1089, 1046, 1033, 851, 802, 755, 660, 483, 456, 395, 355, 317, 217, 243, 198, 160, 148, and 114 cm$^{-1}$. In a preferred embodiment of the present invention, a substantially pure crystalline form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is characterized by an FT-RAMAN spectrum having at least one, more preferably at least two, still more preferably at least four, and most preferably all, of the RAMAN bands noted above. The thermogravimetry and differential thermal analysis (TG-DTA) curve for form B of the hydrochloride salt is shown in FIG. 11.

The x-ray powder diffraction pattern for form B' (anhydrous) of the hydrochloride salt shows at least one, more preferably at least two, still more preferably at least four, and most preferably all, maxima selected from about 7.2°, 9.2°, 11.5°, 12.0°, 13.9°, 14.3°, 15.4°, 17.6°, 18.6°, 20.3°, 21.7°, 22.5°, 23.2°, 24.7°, 24.9°, 25.2°, 26.0°, 26.6°, 27.5°, 28.2°, 29.2° and 30.0° (2θ degrees). A particularly preferred embodiment of the present invention is directed to a substantially pure crystalline form B' of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 12. Exposed to moisture, the anhydrous form B' converts back to the monohydrate. Overall, Form B is favored in solvents with low moisture content (<5%), and form A is favored in solvents with a high moisture content. Form B of the hydrochloride salt can be produced from methanol; however, it appears that it crystallizes first as a methanol solvate (form $S_B$ described further below) which then converts quickly to the monohydrate form B when exposed to air. The methanol solvate does not, however, convert to form B if vacuum dried; air drying suffices for conversion to form B.

An additional embodiment of the present invention is directed to form $S_B$ of the hydrochloride salt, which is a dimethanol solvate corresponding to form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide; this form can be isolated only if protected from ambient conditions, i.e., ambient moisture, which causes conversion to the form B monohydrate hydrochloride salt. The x-ray powder diffraction pattern for form $S_B$ of the hydrochloride salt shows at least one, more preferably at least two, still more preferably at least four, and most preferably all, maxima selected from about 7.5°, 9.3°, 11.5°, 14.8°, 19.4°, 21.9°, 23.0°, 23.8°, 24.9°, 25.6°, 25.9°, 26.3° and 26.7° (2θ degrees). A particularly preferred embodiment of the present invention is directed to a substantially pure crystalline form $S_B$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 13. Another related crystalline form is form $S_B'$, which is believed to be a mono-methanol solvate corresponding to form B. The x-ray powder diffraction pattern for form $S_B'$ of the hydrochloride salt shows at least one, more preferably at least two, still more preferably at least four, and most preferably all, maxima selected from about 7.5°, 9.3°, 11.6°, 12.4°, 13.4°, 13.8°, 14.9°, 19.7°, 20.2°, 22.0°, 23.0°, 23.9°, 24.2°, 25.1°, 26.0°, 26.8°, 29.3° and 30.7° (2θ degrees). A particularly preferred embodiment of the present invention is directed to a substantially pure crystalline form $S_B'$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 14.

Form C of the hydrochloride salt is another monohydrate. In the presence of methanol vapor, form C converts to form B. A DSC scan of form C shows a first endotherm at about 100° C.-120° C. which corresponds to dehydration, i.e., transition to an anhydrous crystalline form C'; DSC also shows a second endotherm at about 180° C. which corresponds to melting. XRPD at various temperatures shows anhydrous form C' between about 155-195° C.; after melting at about 195° C., form C' becomes amorphous upon holding at about 40° C. for about 30 minutes.

Figure 16:
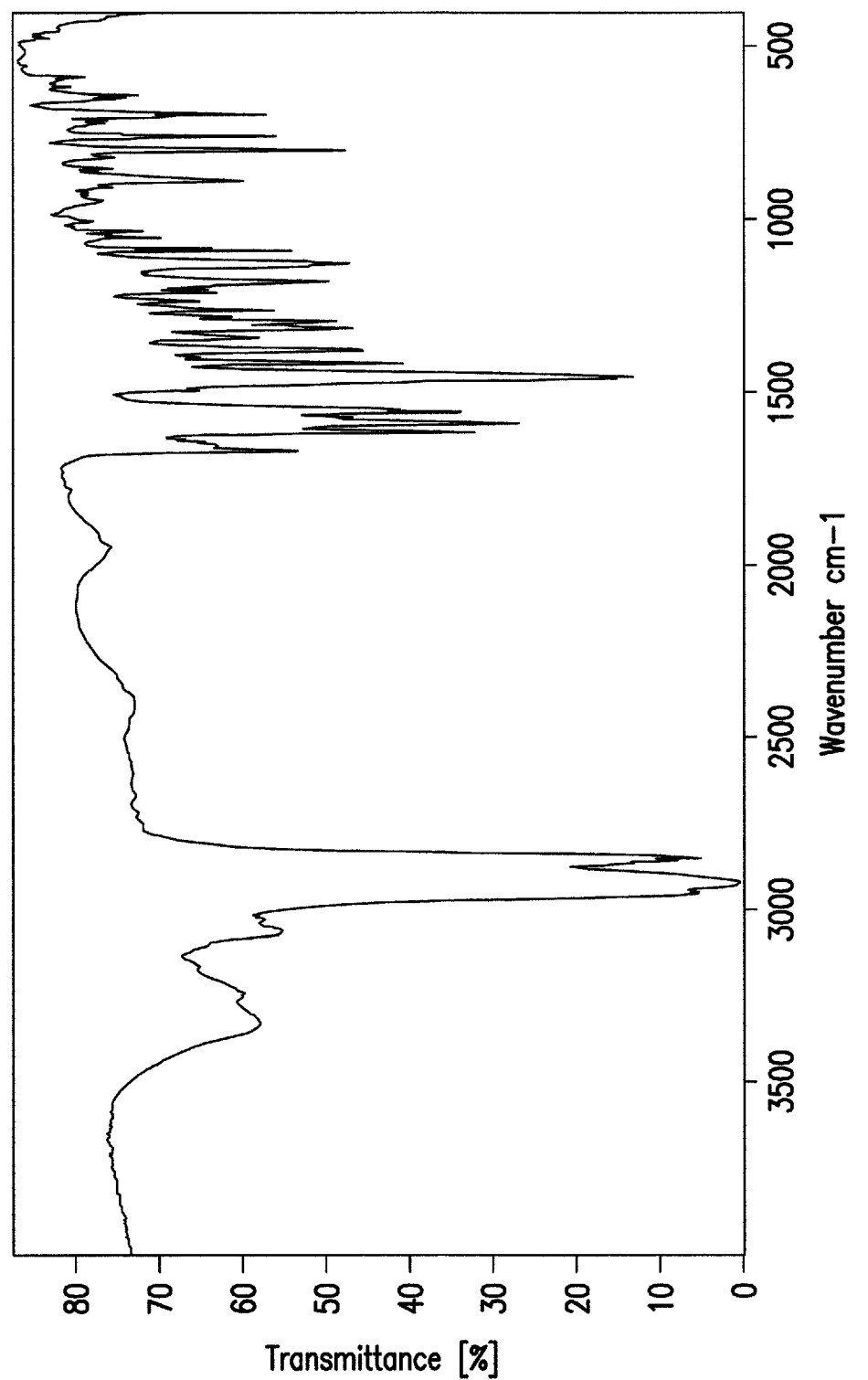
FIG. 16 shows the FT-IR spectrum for form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as recorded in Nujol mull between two KBr plates using a Bruker IFS-55 instrument.
Figure 17:
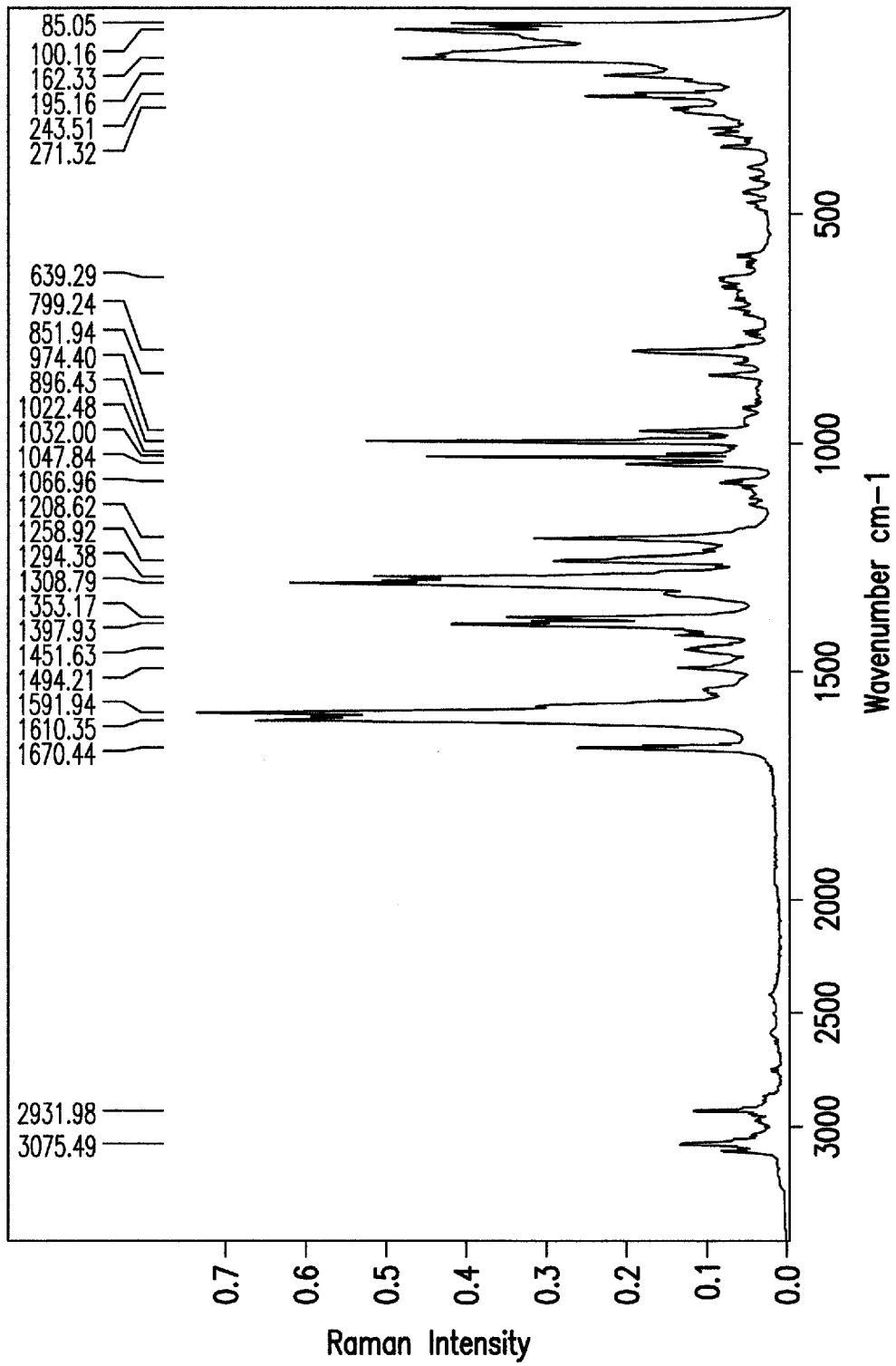
FIG. 17 shows the FT-RAMAN spectrum for form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as recorded using a Bruker RFS-100 instrument.
Figure 18:
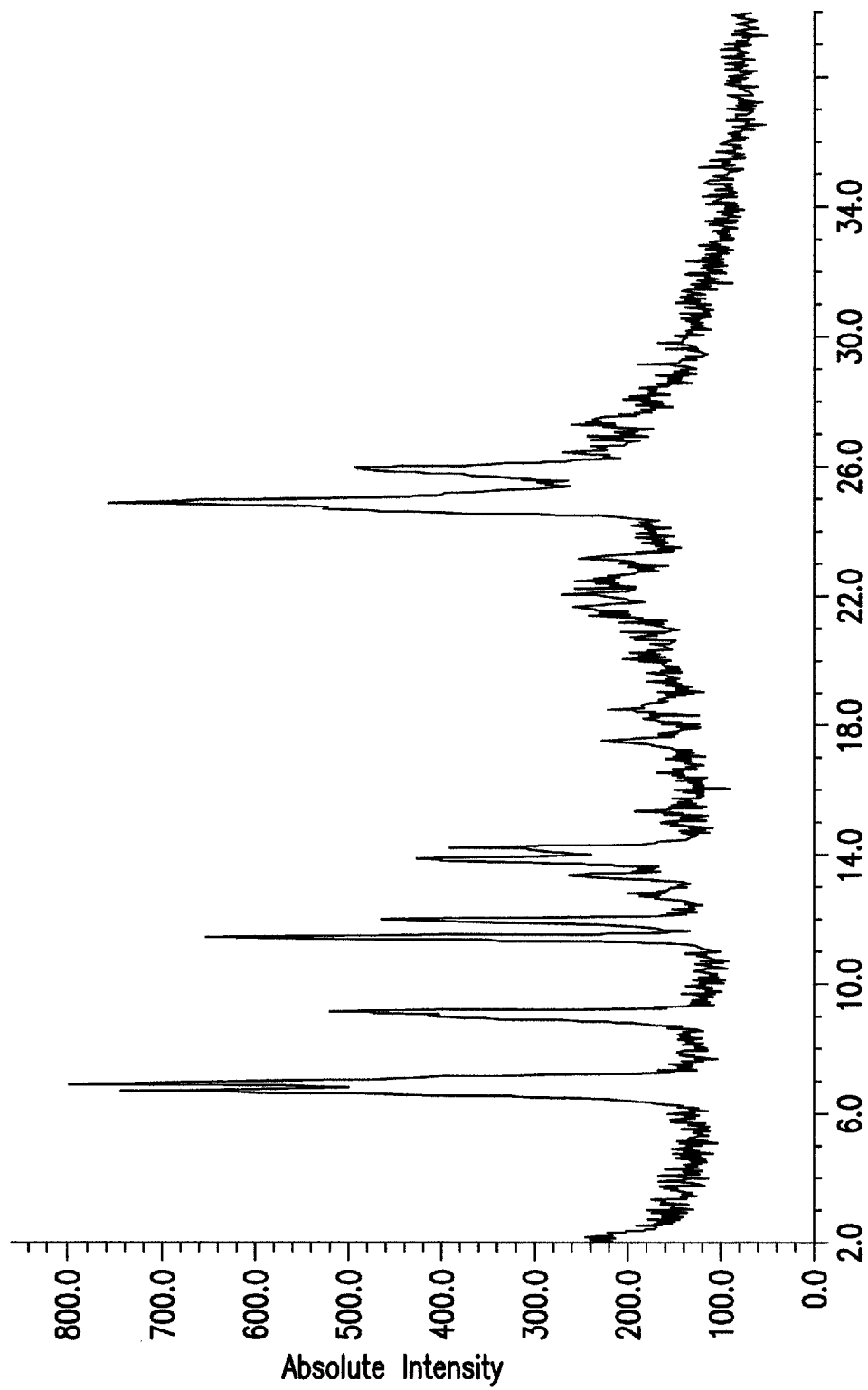
FIG. 18 shows the x-ray powder diffraction pattern for form C' of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 19:
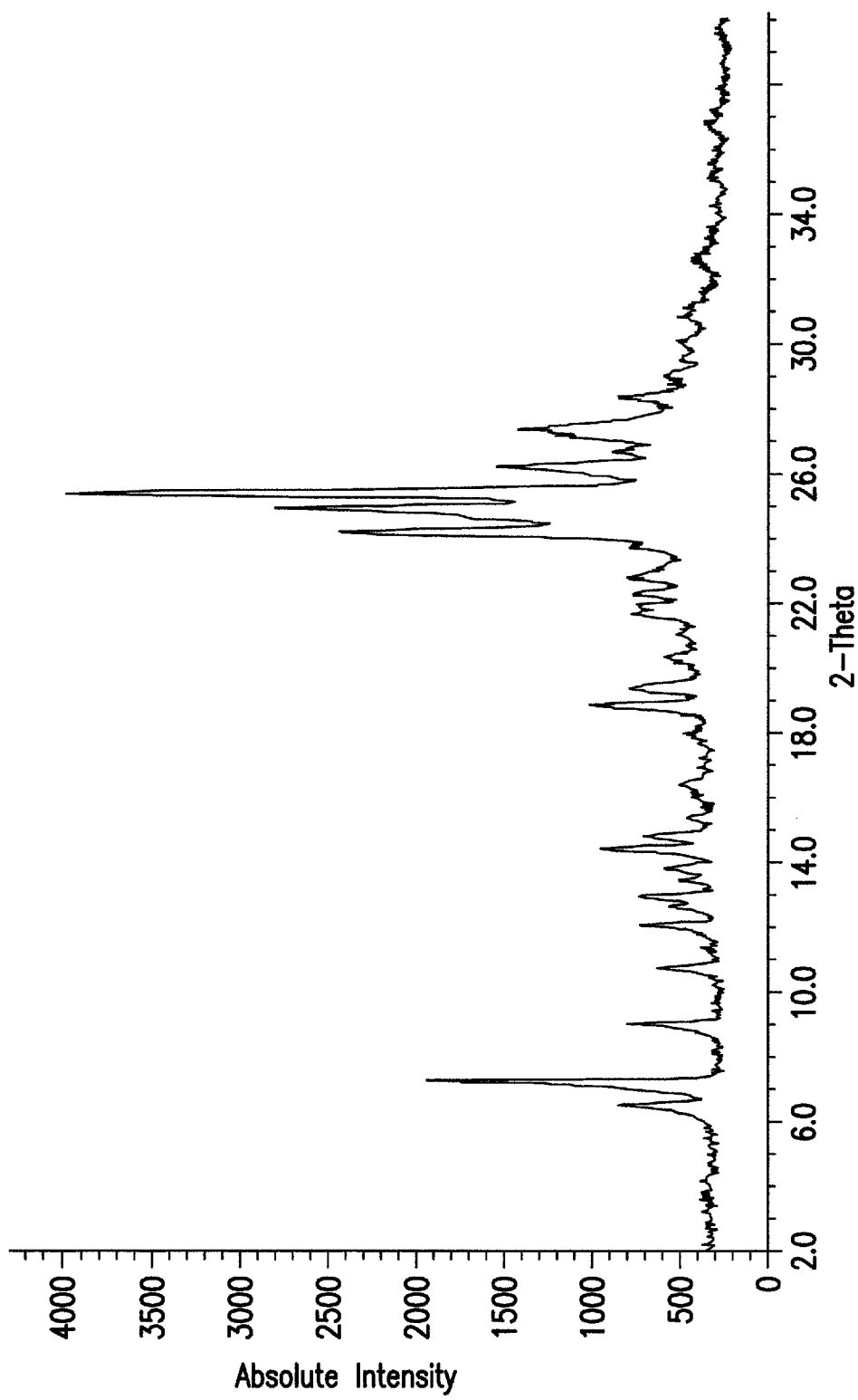
FIG. 19 shows the x-ray powder diffraction pattern for form $S_C$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.

The x-ray powder diffraction pattern for form C of the hydrochloride salt shows at least one, more preferably at least two, still more preferably at least four, and most preferably all, maxima selected from about 6.6°, 7.0°, 8.9°, 11.2°, 11.8°, 13.3°, 14.0°, 17.3°, 18.4°, 20.0°, 22.1° and 23.0° (2θ degrees). A particularly preferred embodiment of the present invention is directed to a substantially pure crystalline form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 15. The FT-IR spectrum of form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is as shown in FIG. 16. The main IR bands are about: 3332, 2925, 2854, 1670, 1615, 1588, 1556, 1455, 1414, 1312, 1293, 1260, 1234, 1179, 1126, 1087, 1087, 1050, 1032, 886, 797, 758, and 696 cm$^{-1.}$ In a preferred embodiment of the present invention, a substantially pure crystalline form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is characterized by an FT-IR spectrum having at least one, more preferably at least two, still more preferably at least four, and most preferably all, of the IR bands noted above. The FT-RAMAN spectrum of form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is as shown in FIG. 17. The main RAMAN bands are about: 3075, 2932, 1670, 1610, 1592, 1494, 1452, 1398, 1383, 1309, 1294, 1259, 1210, 1087, 1047, 1033, 1022, 852, 799, 639, 271, 244, 162, 100, and 85 cm$^{-1}$. In a preferred embodiment of the present invention, a substantially pure crystalline form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is characterized by an FT-RAMAN spectrum having at least one, more preferably at least two, still more preferably at least four, and most preferably all, of the RAMAN bands noted above.

Dehydration of form C leads to an anhydrous crystalline form C'. Form C' converts within a few minutes under room conditions to a mixture of forms B and C. The x-ray powder diffraction pattern for form C' of the hydrochloride salt shows at least one, more preferably at least two, still more preferably at least four, and most preferably all, maxima selected from about 6.7°, 6.9°, 9.1°, 11.4°, 12.0°, 13.8°, 14.2°, 24.8° and 25.8° (2θ degrees). A particularly preferred embodiment of the present invention is directed to a substantially pure crystalline form C' of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 18.

An additional embodiment of the present invention is directed to form $S_C$ of the hydrochloride salt, which is a methanol solvate corresponding to form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide. Form C appears to crystallize first as a methanol solvate (form $S_C$) which then converts quickly to the monohydrate form C when exposed to air. The methanol solvate does not, however, convert to form C if vacuum dried; air drying suffices for conversion to form C. The x-ray powder diffraction pattern for form $S_C$ of the hydrochloride salt shows at least one, more preferably at least two, still more preferably at least four, and most preferably all, maxima selected from about 6.5°, 7.3°, 9.1°, 10.8°, 12.1°, 13.0°, 14.5°, 14.9°, 18.9°, 19.4°, 24.2°, 25.0°, 25.4°, 26.2°, 27.4° and 28.4° (2θ degrees). A particularly preferred embodiment of the present invention is directed to a substantially pure crystalline form $S_C$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 19.

Figure 20:
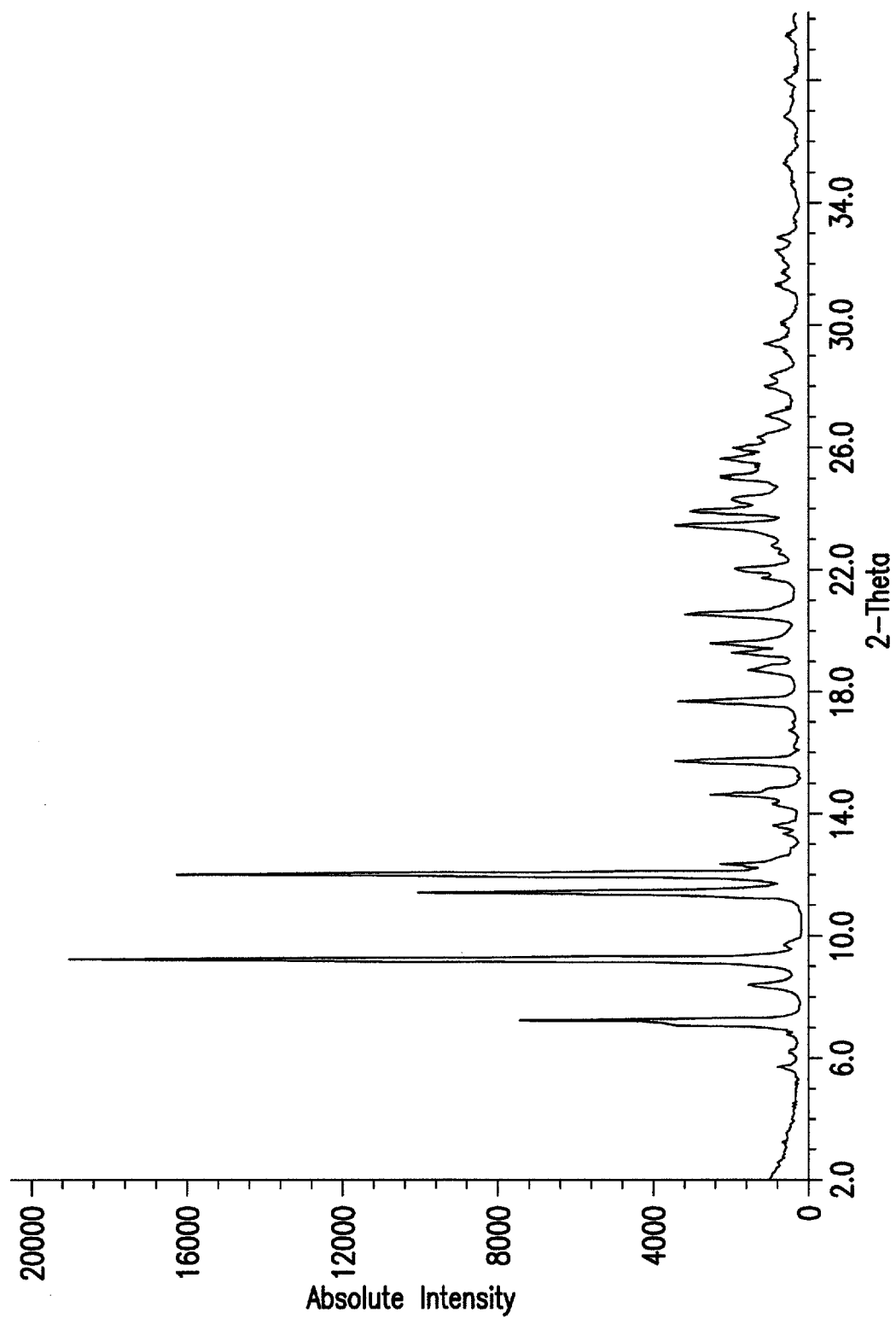
FIG. 20 shows the x-ray powder diffraction pattern for a mixture of form D and form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 21:
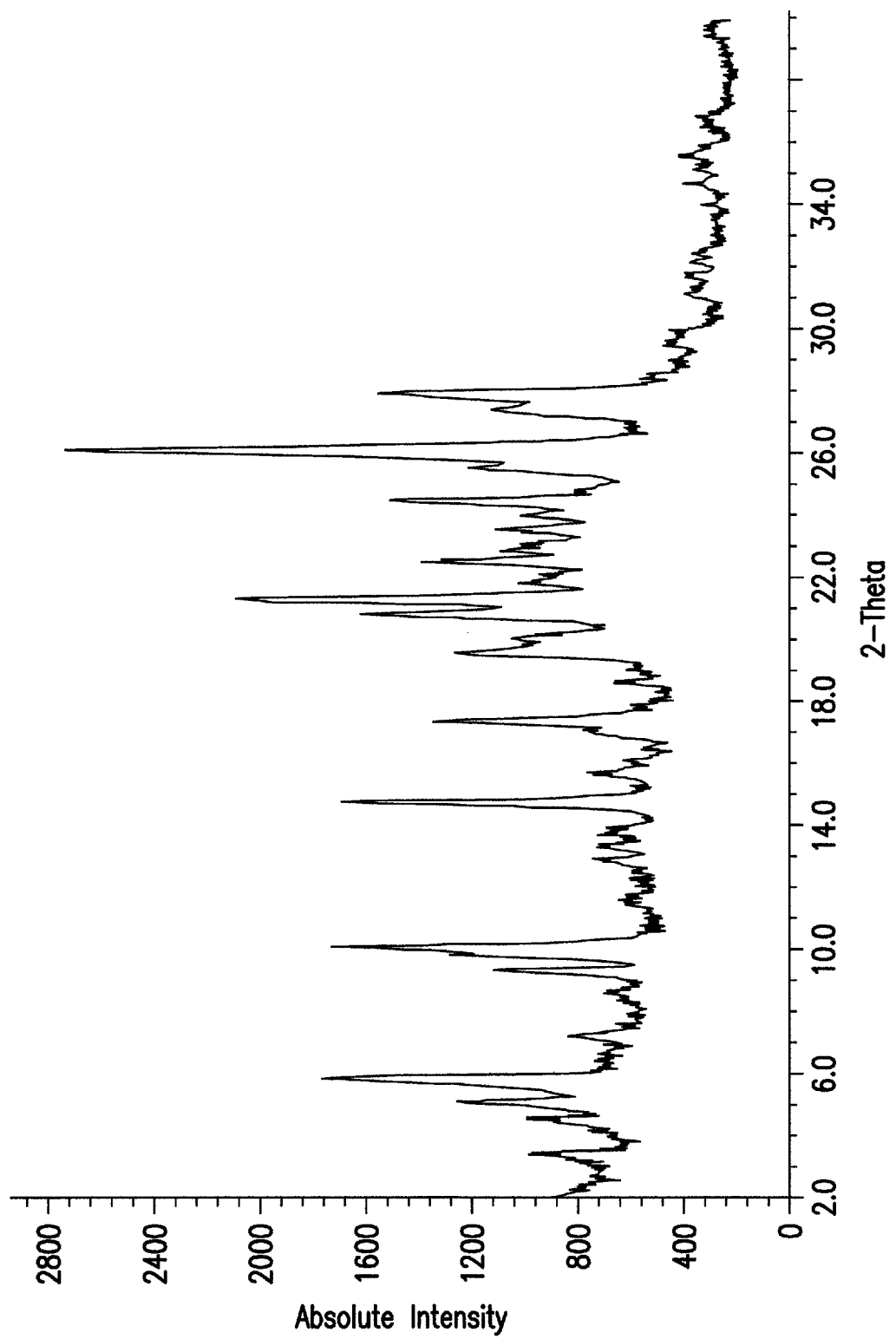
FIG. 21 shows the x-ray powder diffraction pattern for form $S_E$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.

Another crystalline form of the hydrochloride salt is form D. Crystalline form D has thus far been obtained in mixture with form B of the hydrochloride salt. The x-ray powder diffraction pattern for form D of the hydrochloride salt shows at least one, more preferably at least two, and most preferably all, maxima selected from about 5.7°, 8.4° and 9.8° (2θ degrees); the XRPD also shares the maxima of form B noted above due to the presence of form B in mixture with form D. A preferred embodiment of the present invention is directed to a crystalline form D of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as shown in FIG. 20. A more preferred embodiment comprises a substantially pure crystalline form D of the hydrochloride salt.

Still another crystalline form of the hydrochloride salt is form $S_E$, which is a dimethylformamide solvate of the hydrochloride salt. Form $S_E$ can be obtained by treating either form C or the amorphous form of the hydrochloride salt with dimethylformamide vapor at, e.g., 25° C. The x-ray powder diffraction pattern for form $S_E$ of the hydrochloride salt shows at least one, more preferably at least two, still more preferably at least four, and most preferably all, maxima selected from about 3.4°, 4.5°, 5.1°, 5.8°, 7.2°, 9.3°, 10.1°, 12.9°, 13.3°, 13.8°, 14.8°, 15.7°, 17.4°, 19.6°, 20.8°, 21.3°, 22.5°, 24.4°, 25.5°, 26.0°, 27.4° and 27.9° (2θ degrees). A particularly preferred embodiment of the present invention is directed to a substantially pure crystalline form $S_E$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 21.

Figure 22:
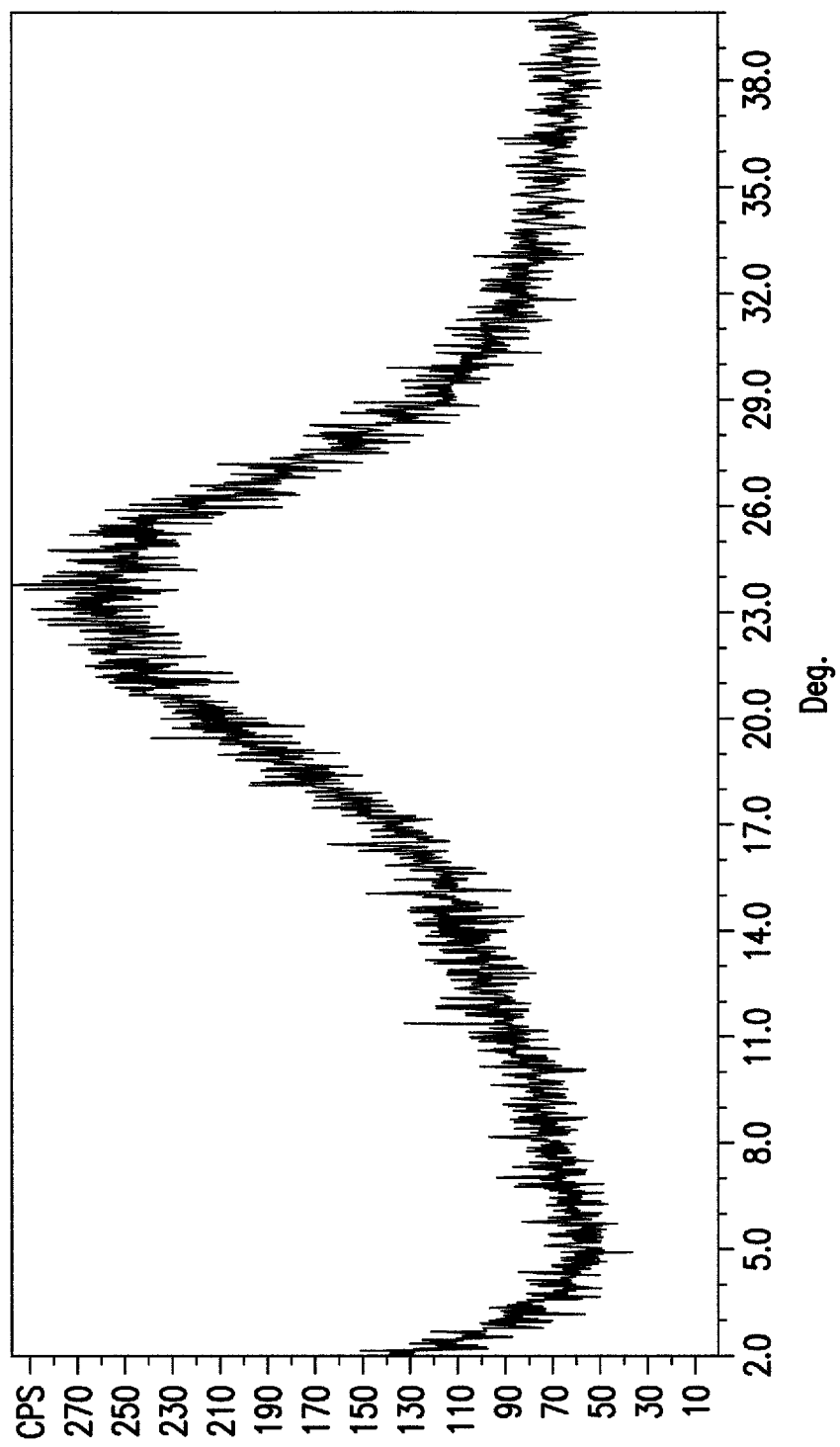
FIG. 22 shows the x-ray powder diffraction pattern (XRPD) for the amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to the present invention.
Figure 23:
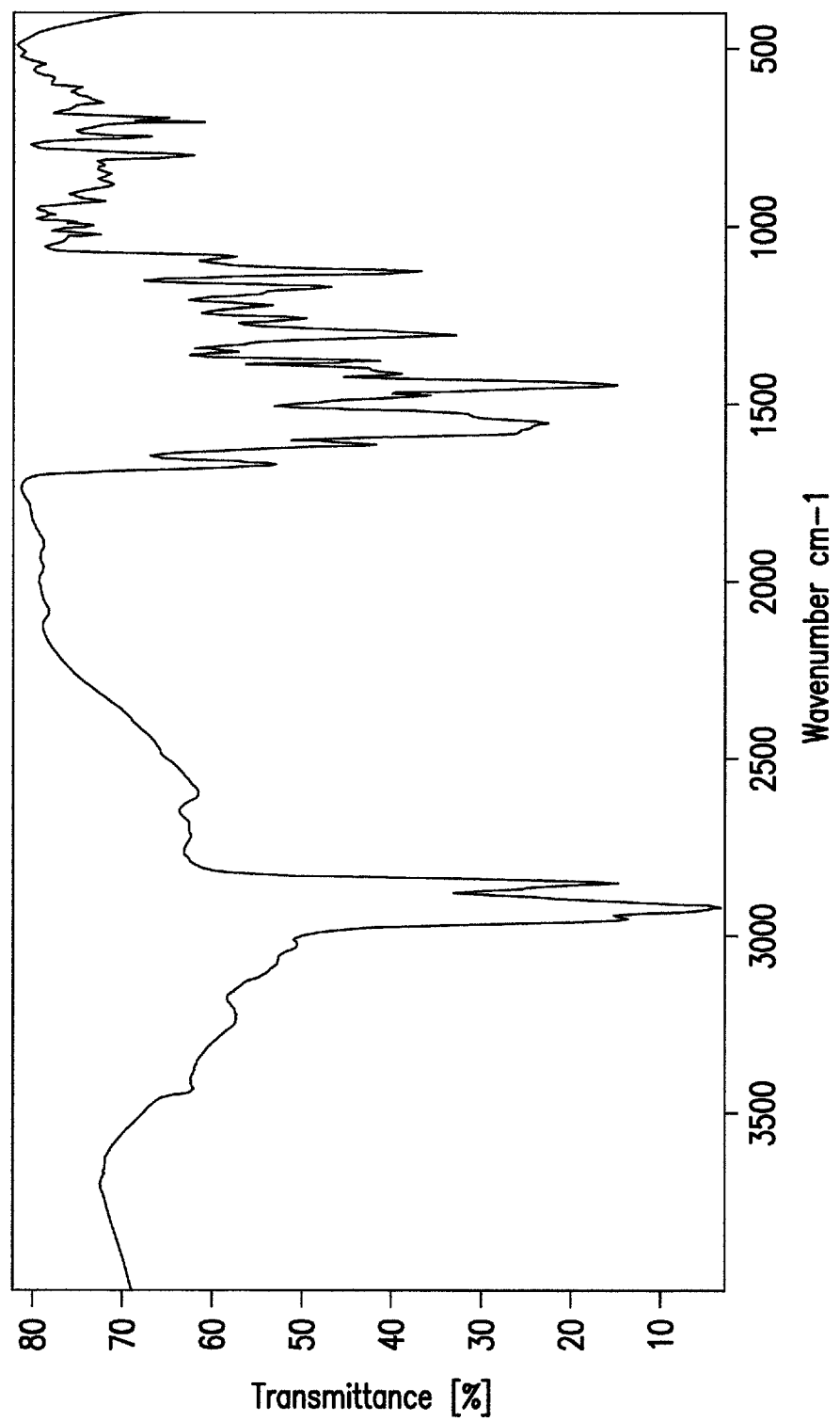
FIG. 23 shows the FT-IR spectrum for the amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as recorded in Nujol mull between two KBr plates using a Bruker IFS-55 instrument.
Figure 24:
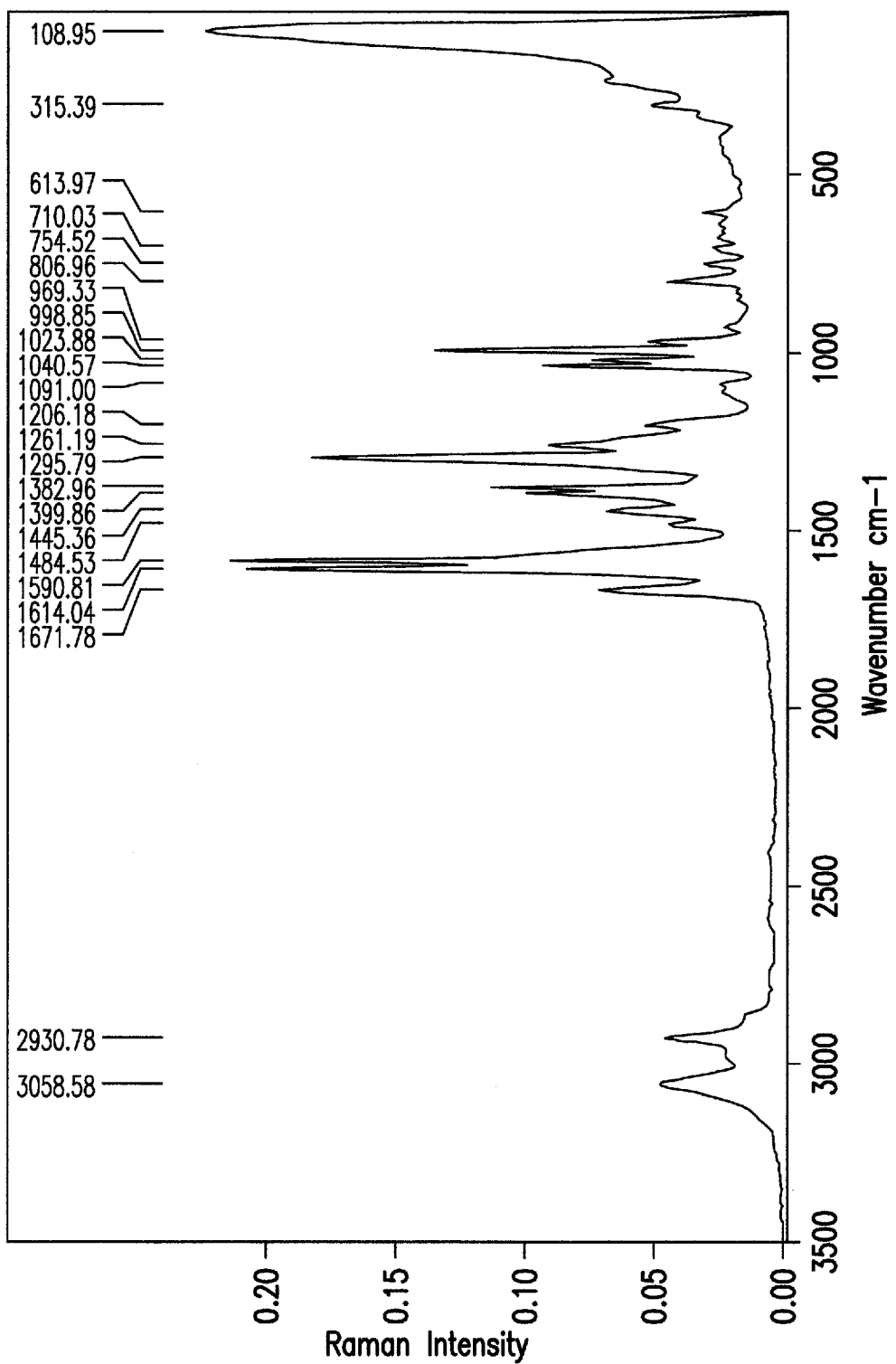
FIG. 24 shows the FT-RAMAN spectrum for the amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as recorded using a Bruker RFS-100 instrument.

In addition to all of the above-noted crystalline forms (i.e., polymorphs, pseudopolymorphs) of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide, the hydrochloride salt also exists in an amorphous form. The amorphous form spontaneously converts to the form A hydrochloride salt after storage at various relative humidities. In the presence of methanol vapor, the amorphous form converts to form B. An XRPD representative of the anhydrous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is shown in FIG. 22. The FT-IR spectrum of the amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is as shown in FIG. 23. The main IR bands are about: 1671, 1615, 1556, 1479, 1447, 1416, 1379, 1354, 1308, 1263, 1225, 1173, 1130, 1025, 1090, 802, 753, 707, and 695 cm$^{-1}$. In a preferred embodiment of the present invention, a substantially pure amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is characterized by an FT-IR spectrum having at least one, more preferably at least two, still more preferably at least four, and most preferably all, of the IR bands noted above. The FT-RAMAN spectrum of the amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is as shown in FIG. 24. The main RAMAN bands are about: 3059, 2931, 1672, 1614, 1591, 1485, 1445, 1400, 1383, 1298, 1261, 1206, 1091, 1041, 1024, 999, 969, 807, 755, 710, 614, 315, and 109 cm$^{-1}$. In a preferred embodiment of the present invention, a substantially pure amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is characterized by an FT-RAMAN spectrum having at least one, more preferably at least two, still more preferably at least four, and most preferably all, of the RAMAN bands noted above.

Form A of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide is another embodiment of this invention. The x-ray powder diffraction pattern for form A of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide shows at least one, more preferably at least two, still more preferably at least four, and most preferably all, maxima selected from about 6.3°, 7.7°, 9.5°, 10.7°, 17.9° and 18.9° (2θ degrees). A particularly preferred embodiment of the present invention is directed to a substantially pure crystalline form A of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 25.

Form B of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide is another embodiment of this invention. The x-ray powder diffraction pattern for form B of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide shows at least one, more preferably at least two, still more preferably at least four, and most preferably all, maxima selected from about 7.3°, 17.7°, 19.0°, 20.2° and 20.8° (2θ degrees). A particularly preferred embodiment of the present invention is directed to a substantially pure crystalline form B of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide as characterized by the XRPD of FIG. 25.

In addition to the above-noted crystalline forms of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide, the sulfate salt also exists in an amorphous form. A preferred embodiment of the present invention comprises a substantially pure amorphous form of the sulfate salt of 4-methyl-N-[3-(4-methyl-imidazol-1-yl)-5-trifluoromethyl-phenyl]-3-(4-pyridin-3-yl-pyrimidin-2-ylamino)-benzamide.

Various methods can be used to achieve the crystalline forms of each of the free base (forms A and B), the hydrochloride salt (forms A, A', A", B, B', $S_B$, $S_B'$, C, C', $S_C$, D and $S_E$) and the sulfate salt (forms A and B) of 4-methyl-N-[3-(4-methyl-imidazol-1-yl)-5-trifluoromethyl-phenyl]-3-(4-pyridin-3-yl-pyrimidin-2-ylamino)-benzamide. Such methods are as set forth above and as set forth in the below-presented examples and include crystallization at room temperature, crystallization from hot saturated solutions, and precipitation by addition of solvent.

Another embodiment of the present invention is directed to a pharmaceutical composition comprising:

(a) a therapeutically effective amount of a substantially pure crystalline form of 4-methyl-N-[3-(4-methyl-imidazol-1-yl)-5-trifluoromethyl-phenyl]-3-(4-pyridin-3-yl-pyrimidin-2-ylamino)-benzamide free base or a salt thereof according to one of the earlier embodiments of the present invention; and (b) at least one pharmaceutically acceptable carrier, diluent, vehicle or excipient.

In a preferred embodiment, the substantially pure crystalline form is form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide. Preferably, more than 50%, more preferably at least 70%, still more preferably at least 80%, and most preferably at least 90%, of the crystalline form present in the composition is of one of the selected forms.

A "therapeutically effective amount" is intended to mean the amount of the inventive crystalline form that, when administered to a subject in need thereof, is sufficient to effect treatment for disease conditions alleviated by the inhibition of protein kinase activity. The amount of a given compound of the invention that will be therapeutically effective will vary depending upon factors such as the disease condition and the severity thereof, the identity of the subject in need thereof, etc., which amount may be routinely determined by artisans of ordinary skill in the art.

The at least one pharmaceutically acceptable carrier, diluent, vehicle or excipient can readily be selected by one of ordinary skill in the art and will be determined by the desired mode of administration. Illustrative examples of suitable modes of administration include oral, nasal, parenteral, topical, transdermal, and rectal. The pharmaceutical compositions of this invention may take any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols.

Yet another embodiment of the present invention is directed to a method of treating a disease which responds to an inhibition of protein kinase activity comprising the step of administering to a subject in need of such treatment a therapeutically effective amount of a substantially pure crystalline form of 4-methyl-N-[3-(4-methyl-imidazol-1-yl)-5-trifluoromethyl-phenyl]-3-(4-pyridin-3-yl-pyrimidin-2-ylamino)-benzamide according to one of the earlier embodiments of the present invention. In a preferred embodiment, the substantially pure crystalline form is form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide. Preferably, more than 50%, more preferably at least 70%, still more preferably at least 80%, and most preferably at least 90%, of the crystalline form administered is of one of the inventive forms. As noted above, illustrative modes of administration include oral, nasal, parenteral, topical, transdermal, and rectal. Administration of the crystalline form may be accomplished by administration of a pharmaceutical composition of this invention or via any other effective means.

Specific embodiments of the invention will now be demonstrated by reference to the following examples. It should be understood that these examples are disclosed solely by way of illustrating the invention and should not be taken in any way to limit the scope of the present invention.

EXAMPLE 1

About 100 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base is equilibrated with 2 mL of seven different solvents (methanol, ethanol, 2-propanol, ethyl acetate, acetone, tetrahydrofuran, and acetonitrile) for at least 48 hours at room temperature. No form transition occurred.

EXAMPLE 2

About 50 mg of form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is equilibrated with 1 mL of a listed solvent for at least 20 hours in a water bath at 25° C.±0.5 (Table 3) and 50° C.±0.5 (Table 4). Then the solutions are filtered and dried for 10 minutes in the air. The solid part is then investigated by XRPD. If differences are observed, additional investigations are performed (DSC, TGA, infrared (IR), scanning election microscope (SEM)). The approximate solubility in the solvent is determined after evaporation of the solvent in vacuum by gravimetry.

TABLE 3

Equilibration with Solvents at 25° C.

| Solvent | Solubility (mg/g) | Form |
|---|---|---|
| Acetone | 0.2 | B |
| Acetonitrile | 0.3 | B |
| Ethanol (96%) | 3.9 | B |
| Ethyl acetate | 0.3 | B |
| Methanol | 16.3 | B |
| Propan-2-ol | 1.5 | B |
| Toluene | 1.3 | B |
| Tetrahydrofuran | 5.8 | B |
| Tetrahydrofuran-water 1:1 | 12.2 | A |
| Acetonitrile-water 1:1 | 10.3 | A |
| Water | 0.2 | B |

TABLE 4

Equilibration with Solvents at 50° C.

| Solvent | Solubility (mg/g) | Form |
|---|---|---|
| Acetone | 1.0 | B |
| Acetonitrile | 2.1 | B |
| Ethanol (96%) | 22.4 | B |
| Ethanol | 26.5 | B |
| Ethyl acetate | 3.0 | B |
| Propan-2-ol | 4.8 | B |
| Toluene | 5.6 | B |
| Ethanol-water 1:1 | 17.2 | B |
| Methanol | >27.5 | Solvate (as wet cake - dries to B) |
| DMSO | >27.5 | — (too soluble) |

EXAMPLE 3

Mixtures of forms A and B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide were equilibrated in various solvents.

TABLE 5

Equilibration of A-B Mixtures

| Solvent | Form | Comments |
|---|---|---|
| Ethanol (95%) | B | After 72 hours |
| Methanol 2% water | B | 24 hours 40° C. |
| Methanol 0.25% water | B/? | 24 hours 40° C., extra peaks not form A - maybe free base polymorph |
| Methanol 2% water | B | 40 hours 5° C. |
| Methanol 0.25% water | B | 40 hours 5° C. |
| Methanol 10% water | A/B | Significant enrichment in A after 12 hours |
| Methanol 2% water | B | Rapid evaporation of filtrate from 24 hours 40° C. |
| Tetrahydrofuran 15% water | A | |

? = extra peak (unclear whether new form or free base)

EXAMPLE 4

The residue (hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide) from Example 2 can be examined for its crystalline form upon evaporation at room temperature. The results are shown in Table 6 below.

TABLE 6

Evaporation at Room Temperature

| Solvent | Form |
|---|---|
| Acetone | Amorphous |
| Acetonitrile | Amorphous |
| Ethanol (96%) | A & B |
| Ethyl Acetate | B |
| Methanol | B |
| Propan-2-ol | B |
| Toluene | B |
| Tetrahydrofuran | Amorphous |
| Tetrahydrofuran-water (50:50) | A |
| Acetonitrile-water (50:50) | A |
| Ethanol-water (50:50) | A |
| Methanol-water (50:50) | A |

EXAMPLE 5

Approximately 300 mg of form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide are dissolved in the minimal amount of solvent at 60° C. No remaining crystals should be visible. Then the solutions are cooled in an ice bath and agitated. The precipitates are collected on a filter, dried and investigated by XRPD.

TABLE 7

Crystallization from Hot Saturated Solutions

| Solvent | $T_1/T_2$(° C.) | Form | Notes |
|---|---|---|---|
| Methanol-water (15%) | 50-10 | B | Shifted peaks due to hydration |
| Methanol | 40-5 | B | |
| Methanol-water (2%) | 40-10 | B | Crash cool |
| Tetrahydrofuran | 50-10 | No results | |
| Tetrahydrofuran | 50-10 | No results | 1% water |
| Ethanol | 50-10 | No results | No crystallization |
| Ethanol | 50-10 | A & B | After 2% water and B seeds added |
| Ethanol (95%) | 50-10 | A | |
| Ethanol (succinic acid) | 50-10 | A | 100% ethanol used |
| Ethanol (malonic acid) | 50-10 | B | 100% ethanol used |
| Isopropyl alcohol | 50-10 | A | Poor crystallinity |
| Tetrahydrofuran-water (15%) | 50-10 | A | |
| Tetrahydrofuran-water (15%) | 50-10 | A | B seeds |

EXAMPLE 6

Two different solvent combinations are tested. Form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is dissolved in a medium where the solubility is high, and a solvent in which the salt is highly insoluble is added. The precipitates are collected on a filter, dried and investigated by XRPD.

TABLE 8

Precipitation by Addition of Solvent

| Solvent | Solvent added | Form |
|---|---|---|
| Tetrahydrofuran-water | Ethyl acetate | A |
| Methanol-water | Acetonitrile | A |

EXAMPLE 7

300 mg of form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide are compressed for 5 minutes at 10 tons with a hydraulic press (diameter of tablets=13 mm). There was no change of crystalline modification (by XRPD) after compression for 5 minutes at room temperature. However, the XRPD peaks are much broader indicating less crystallinity.

EXAMPLE 8

Granulating solvent is added dropwise to form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide until the solid is wetted sufficiently. The material is vortexed between each addition. Then the material is dried under vacuum to <2% or less and evaluated for form and degree of crystallinity by XRPD or DSC.

TABLE 9

| Granulating solvent | XRPD results |
|---|---|
| Water | No change |
| Ethanol | No change |

EXAMPLE 9

Amorphous 4-methyl-N-[3-(4-methyl-imidazol-1-yl)-5-trifluoromethyl-phenyl]-3-(4-pyridin-3-yl-pyrimidin-2-ylamino)-benzamide hydrochloride was crystallized in acetonitrile to form a mixture of form A of the hydrochloride salt and form A of the free base. Amorphous 4-methyl-N-[3-(4-methyl-imidazol-1-yl)-5-trifluoromethyl-phenyl]-3-(4-pyridin-3-yl-pyrimidin-2-ylamino)-benzamide hydrochloride was crystallized in isopropanol to form a mixture of form A of the hydrochloride salt and a small amount of form A of the free base.

EXAMPLE 10

About 50-60 mg of form A of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 0.75 mL of a listed solvent. The stoichiometric amount of hydrochloric acid was subsequently added to the suspension, which became less viscous after the addition. The mixture was stirred at ambient temperature for about 5 hours. Solids (salts) were collected by filtration and analyzed by XRPD and NMR.

TABLE 10

| Solvent | Results | |
|---|---|---|
| | Crystallinity* | $^1$H-NMR |
| Methanol | Good; form B | No solvent peak |
| Ethanol | Good; forms A & B | No solvent peak |
| 2-propanol | Good; form A | No solvent peak |
| Acetone | Excellent; form A | Not performed |
| Ethyl acetate | Good; form A & B | Not performed |
| Tetrahydrofuran | Excellent; form A | Not performed |
| acetonitrile | Excellent; form A & B | Not performed |

*excellent = when main peaks are sharp and their intensities above 70 counts
good = when main peaks are sharp and their intensities within 30-70 counts

EXAMPLE 11

About 50-60 mg of form A of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 0.75 mL of a listed solvent. The stoichiometric amount of $H_2SO_4$ was subsequently added to the suspension, which became less viscous after the addition. The mixture was stirred at ambient temperature for about 5 hours. Solids (salts) were collected by filtration and analyzed by XRPD and, in some cases, also by NMR.

TABLE 11

| Solvent | Results | |
|---|---|---|
| | Crystallinity* | $^1$H-NMR |
| Methanol | Good; forms A & B | No solvent peak |
| Ethanol | Good; form B | No solvent peak |
| 2-propanol | Poor | Not performed |
| Acetone | Poor | Not performed |
| Ethyl acetate | Poor | Not performed |
| Tetrahydrofuran | Poor | Not performed |
| acetonitrile | Poor | Not performed |

*good = when main peaks are sharp and their intensities within 30-70 counts
poor = when main peaks are broad and their intensities below 30 counts

EXAMPLE 12

About 300 to 310 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 9 mL of 2-propanol. The stoichiometric amount of HCl was subsequently added to the suspension. After addition, the slurry became yellow, then off-white. The mixture was stirred at ambient temperature for about 5 hours. After 4 hours of holding, the slurry was paste-like, difficult to pour and filter. The solid was collected by filtration and analyzed by XRPD and NMR. The XRPD showed good crystallinity and form A of the hydrochloride salt, while the $^1$H-NMR showed both changed shifts and no solvent peak.

EXAMPLE 13

About 300 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 30 mL of methanol. The suspension was heated to the reflux temperature of 64° C.; the slurry became clear under reflux. The stoichiometric amount of $H_2SO_4$ dissolved in methanol was subsequently added to the suspension. The solution was stirred under reflux for 5 hours and then cooled to ambient temperature; the solid precipitated out after holding. The solid was collected by filtration and analyzed by XRPD. The XRPD showed form B of the sulfate salt.

EXAMPLE 14

About 100 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 15 mL of methanol. The stoichiometric amount of the listed acid was subsequently added to the suspension. The solution was stirred at 50° C. for about 5 hours and then cooled to ambient temperature. Solids (salts) were collected and analyzed by XRPD and NMR.

TABLE 12

| Acid | Comments | Results | |
|---|---|---|---|
| | | Crystallinity | $^1$H-NMR |
| HCl | The slurry became clear while heating and remained so. Slow $N_2$ flow was used to evaporate some solvent. | Good; form B | Shifts changed; no solvent peak |
| $H_2SO_4$ | The slurry became clear after heating. It became slurry during cooling. | Good; forms A & B | Shifts changed; <2% methanol |

EXAMPLE 15

About 100 mg of form B of 4-methyl-N-[3-(4-methyl-imidazol-1-yl)-5-trifluoromethyl-phenyl]-3-(4-pyridin-3-yl-pyrimidin-2-ylamino)-benzamide free base was suspended in 15 mL of methanol. Listed amount of the listed acid was subsequently added to the suspension. The solution was stirred at ambient temperature (HCl) or 50° C. ($H_2SO_4$) for about 5 hours. The solids (salts) were obtained by evaporating solvent to dryness using a slow $N_2$ flow and analyzed by XRPD and NMR.

TABLE 13

| Acid | Comments | Results | |
|---|---|---|---|
| | | Crystallinity | 1H-NMR |
| 1 equivalent HCl | The slurry became clear while heating and remained so. | Good; form B of HCl salt | Shifts changed; no solvent peak |

TABLE 13-continued

| | | Results | |
|---|---|---|---|
| Acid | Comments | Crystallinity | 1H-NMR |
| 0.5 equivalents $H_2SO_4$ | The slurry became clear while heating and remained so. | Good; form A of sulfate salt & free base form B | Shifts changed; small solvent peak |
| 1 equivalent $H_2SO_4$ | The slurry became clear after acid addition and remained so. | Good; form A of sulfate salt | Shifts changed; no solvent peak |

EXAMPLE 16

A 1 L, 4-neck, round-bottom flask equipped with a mechanical stirrer, a thermometer, heating/cooling capacity, and an addition funnel was charged in sequence with 4-methyl-N-[3-(4-methyl-imidazol-1-yl)-5-trifluoromethyl-phenyl]-3-(4-pyridin-3-yl-pyrimidin-2-ylamino)-benzamide free base (10 g), methanol (250 mL), and 37% hydrochloric acid (1.85 g) under nitrogen purge. The mixture was heated to 42-50° C. and stirred for an additional 15 minutes. The resulting solution was filtered through a polypropylene pad, while maintaining the batch temperature above 40° C. The clear solution was transferred under nitrogen atmosphere to another 1 L, 4-neck, round-bottom flask equipped with a mechanical stirrer, a thermometer, and heating/cooling capacity. The batch was stirred and cooled to 30° C. over a period of 30 minutes. Seeds (20 mg) were added at this temperature, and the batch was cooled to 23° C. over a period of 45 minutes. The batch was stirred for an additional 3 hours to obtain a thick white suspension. The suspension was cooled to −10° C. over a period of 1.5 hours and stirred for an additional 30 minutes. Any solid was collected by filtration and rinsed with cold (−10° C.) methanol (20 mL). The solid was dried at 50-55° C./10-20 torr for 8-16 hours to obtain 4-methyl-N-[3-(4-methyl-imidazol-1-yl)-5-trifluoromethyl-phenyl]-3-(4-pyridin-3-yl-pyrimidin-2-ylamino)-benzamide monohydrochloride monohydrate salt form B (9.8 g) as a white solid.

$^1$H NMR 300 MHz, DMSO-d6), δ 10.9 (s, 1H), 9.58 (s, 1H), 9.29 (s, 1H), 9.20 (s, 1H), 8.70 (d, 1H), 8.63 (s, 1H), 8.55 (d, 1H), 8.49 (d, 1H), 8.32 (d, 2H), 8.00 (s, 1H), 7.91 (s, 1H), 7.84 (d, 1H), 7.56-7.44 (m, 3H), 2.50 (s, 3H), 2.35 (s, 3H); x-ray diffraction pattern showing maxima at 2θ=7.4°, 9.4°, 11.6°, 12.1°, 15.8°, 19.3°, 19.6°, 22.1°, 24.1°, 25.7°.

EXAMPLE 17

Separately about 100 mg of form A and form B of 4-methyl-N-[3-(4-methyl-imidazol-1-yl)-5-trifluoromethyl-phenyl]-3-(4-pyridin-3-yl-pyrimidin-2-ylamino)-benzamide free base was equilibrated with 2 mL of thirteen different solvents (acetone, acetonitrile, diethylether, ethanol absolute, ethyl acetate, methanol, propan-2-ol, toluene, tetrahydrofuran, water, tetrahydrofuran/water (1:1), ethanol/water (1:1), and methanol/water (1:1)) for one day in a water bath at 25° C. Then the solutions were filtered and dried for 10 minutes in the air. The solid part was investigated by XRPD. No form transitions occurred with the exception of one trial of form B in water; in one instance, a mixture of free base forms A and B resulted, but those results could not be reproduced.

In addition, about 100 mg of a mixture of form A and form B of 4-methyl-N-[3-(4-methyl-imidazol-1-yl)-5-trifluoromethyl-phenyl]-3-(4-pyridin-3-yl-pyrimidin-2-ylamino)-benzamide free base was equilibrated with 2 mL of seven different solvents (ethanol absolute, methanol, tetrahydrofuran, water, tetrahydrofuran/water (1:1), ethanol/water (1:1), and methanol/water (1:1)) for one day in a water bath at 25° C. Then the solutions were filtered and dried for 10 minutes in the air. The solid part was investigated by XRPD. No form transitions occurred.

EXAMPLE 18

Solubility for each of form A, form B and a mixture of form A and B free base were determined from a saturated solution at 25° C. The results are listed in Table 14 below.

TABLE 14

| Solvent | form A (mg/mL) | form B (mg/mL) | form A/form B (1:1) (mg/mL) |
|---|---|---|---|
| Water | 0.00 | 0.00 | 0.00 |
| Tetrahydrofuran/water (1:1) | 1.78 | 1.95 | 1.93 |
| Ethanol/water (1:1) | 0.06 | 0.07 | 0.07 |
| Methanol/water (1:1) | 0.01 | 0.01 | 0.01 |

As can be seen, form A of the free base has a lower solubility at 25° C. as compared to form B of the free base in the different solvent mixtures. Solubility was too low to perform proper comparison in water.

EXAMPLE 19

12 g 4-methyl-N-[3-(4-methyl-imidazol-1-yl)-5-trifluoromethyl-phenyl]-3-(4-pyridin-3-yl-pyrimidin-2-ylamino)-benzamide hydrochloride is dissolved in 192 mL of methanol and 21 ml of water at 52° C. The solution is heated to 64-66° C. in 10 minutes and let stand for 45 minutes. The solution is then cooled down in 3 hours at 0° C. The solution spontaneously crystallized before 0° C.; therefore, the cooling ramp was stopped at 20° C. and let stand with stirring for 2 days. The suspension is cooled down to 0° C. in 2 hours before filtration under vacuum to obtain form A of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide.

EXAMPLE 20

4-Methyl-N-[3-(4-methyl-imidazol-1-yl)-5-trifluoromethyl-phenyl]-3-(4-pyridin-3-yl-pyrimidin-2-ylamino)-benzamide hydrochloride form B is prepared by suspending free base in methanol at room temperature or at 50° C. 1.06 equivalent of 37% aqueous hydrochloric acid is added, and the mixture is heated to reflux (64° C.) to give a solution that is clarified by filtration. The clarified solution is then cooled to 42° C. and seeded with 0.1% seeds per base. The seeds are suspended in a mixture of 99% methanol and 1% water. The suspension is stirred at 42° C. for 2.5 hours and afterwards cooled down to −10° C. according to a slow cooling profile. At 20° C., the cooling is interrupted for four hours in order to let a potentially formed methanol solvate transform to the desired monohydrate.

The suspension is filtered and washed with two portions of methanol/water mixture (99% methanol/1% water). The filter cake is dried in an oven at 70° C. under a vacuum below 10 mbar overnight. The water content after filtration was found to be below the theoretical value of 3.05% for 50 g scale and above. To assure the correct water content, a second drying stage is added where water is evaporated in a stirred vessel and transported to the dryer by a vacuum pump. The conditions in the dryer are changed to 60° C. and 30 mbar in order to assure adequate conditions for the desired water content. The water is added until the saturation capacity is reached.

With the described method, a water content of 3.5-3.6% was obtained with two lab scale (1 L) paddle dryer experiments.

EXAMPLE 21

1.2 mg 4-methyl-N-[3-(4-methyl-imidazol-1-yl)-5-trifluoromethyl-phenyl]-3-(4-pyridin-3-yl-pyrimidin-2-ylamino)-benzamide hydrochloride is placed in 120 mg of methanol and 12 mg of water. A clear solution is obtained at room temperature. An additional 12 g 4-methyl-N-[3-(4-methyl-imidazol-1-yl)-5-trifluoromethyl-phenyl]-3-(4-pyridin-3-yl-pyrimidin-2-ylamino)-benzamide hydrochloride is added, and the suspension is let stand for 1 hour at room temperature. The seeding suspension is placed 10 seconds in an ultrasonic water bath.

4-Methyl-N-[3-(4-methyl-imidazol-1-yl)-5-trifluoromethyl-phenyl]-3-(4-pyridin-3-yl-pyrimidin-2-ylamino)-benzamide hydrochloride (12 g) is suspended in 192 mL of methanol and 14.87 mL of water. The solution is heated to 64-66° C. in 10 minutes and kept for 5 minutes at 66° C. The solution is then cooled down to 42° C. in 15 minutes and then seeded. The suspension is kept for 2.5 hours at 42° C. and cooled down to 20° C. in 7 hours and cooled down within 6 hours at -10° C. The suspension is kept for 79 hours before filtration under vacuum. The solid is washed 2 times with a cold mixture of methanol/water 66 mL/5.26 mL (-10° C.) and dried under vacuum at 70° C. for 20 hours to obtain form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide.

EXAMPLE 22

4-methyl-N-[3-(4-methyl-imidazol-1-yl)-5-trifluoromethyl-phenyl]-3-(4-pyridin-3-yl-pyrimidin-2-ylamino)-benzamide hydrochloride (14 g) is dissolved in 1,000 g of methanol in a hot water bath. The solution is spray dried in a Buchi Mini spray at about 65° C. to form the amorphous hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide.

EXAMPLE 23

4.0 g 4-methyl-N-[3-(4-methyl-imidazol-1-yl)-5-trifluoromethyl-phenyl]-3-(4-pyridin-3-yl-pyrimidin-2-ylamino)-benzamide free base is dissolved in 60 mL methanol at 50° C. 1.05 equivalent (688.7 µL) of hydrochloric acid is added as a solution in 2 mL of methanol. The solution is let stand for 60 minutes at 50° C. The solution is cooled down to 42° C. and kept at this temperature for 15 minutes. A suspension of 4 mg of 4-methyl-N-[3-(4-methyl-imidazol-1-yl)-5-trifluoromethyl-phenyl]-3-(4-pyridin-3-yl-pyrimidin-2-ylamino)-benzamide hydrochloride in methanol (40mg)/water (0.4 mg) homogenized for 10 seconds in an ultrasonic bath is added. The suspension is let stand for 2.5 hours at 42° C., then cooled down in 7 hours at 20° C. The suspension remains at 20° C. for 56 hours. The suspension is not filtrated before analysis. The dimethanol solvate form $S_B$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is obtained.

EXAMPLE 24

36.0 g 4-methyl-N-[3-(4-methyl-imidazol-1-yl)-5-trifluoromethyl-phenyl]-3-(4-pyridin-3-yl-pyrimidin-2-ylamino)-benzamide hydrochloride is dissolved in a solvent mixture of 576 mL of methanol and 44.61 mL of water at 52° C. The solution is heated up to 64-66° C. in 15 minutes and kept for 5 minutes at 66° C. Then the solution is cooled down at 42° C. in 15 minutes and the solution is seeded. The suspension is kept for 2.5 hours at 42° C., cooled down within 7 hours at 20° C., and maintained at this temperature for 11 hours. The methanol solvate form $S_C$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is obtained.

The seed solution was obtained from 3.6 mg of hydrochloride 4-methyl-N-[3-(4-methyl-imidazol-1-yl)-5-trifluoromethyl-phenyl]-3-(4-pyridin-3-yl-pyrimidin-2-ylamino)-benzamide dissolved in a methanol/water solution (360 mg/36 mg). To the solution, an additional 36 mg of 4-methyl-N-[3-(4-methyl-imidazol-1-yl)-5-trifluoromethyl-phenyl]-3-(4-pyridin-3-yl-pyrimidin-2-ylamino)-benzamide are added. The suspension is maintained for 1 hour at room temperature, and the suspension is placed in an ultrasonic bath for 10 seconds.

EXAMPLE 25

Separately about 100 mg of form A, form B and form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide was equilibrated with 2 mL of 10 different solvents (ethanol, methanol, water, ethanol/water (99:1), methanol/water (99:1), methanol/water (99.3:0.7), methanol/HCl 0.1 N, diethylether, hexane, tetrahydrofuran) for one day in a water bath at 25° C. Then the solutions were filtered and the solid part investigated by XRPD.

In methanol, form A transitioned to form B, and in methanol/water (99:1), form A transitioned to form C with a small amount of form B; in methanol/water (99.3:0.7) and in methanol/HCl 0.1 N, form A transitioned to form B with a small amount of form C. No form transitions occurred for form B. In methanol, form C transitioned to form B and in water, form C transitioned to form A.

Similar equilibration studies were done at 50° C. for 1 day for forms A and C and for 2 days for form B. In methanol, form A transitioned to a mixture of forms B and C, and in each of methanol/water (99:1), methanol/water (99.3:0.7) and methanol/HCl 0.1 N, form A transitioned to form C. Form B transitioned to a mixture of forms A and B in ethanol. In methanol, form C transitioned to form B and in water, form C transitioned to form A; also in ethanol/water (99:1), form C transitioned to a mixture of all three forms and in tetrahydrofuran to a mixture of forms B and C.

EXAMPLE 26

About 100 mg of form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is dissolved in about 2 mL of a solvent listed below at 60° C. The solution is cooled down to -10° C. The suspension is filtered and the solid analyzed.

TABLE 15

| | Modification Obtained by XRPD | | |
|---|---|---|---|
| Solvent | 2 hours | 12 hours | 24 hours |
| Methanol | / | B | B |
| Methanol/water (99.5/0.5) | / | B | B |
| Methanol/water (99.3/0.7) | / | B | B |
| Methanol/water (99.0/1.0) | / | B | B |
| Methanol/water (95.0/5) | B | B | B |

/ = no crystallization observed

EXAMPLE 27

About 100 mg of form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is dissolved in about 2 mL of a solvent listed below at 60° C. The solution is cooled down to 20° C. The suspension is centrifuged but the solid is not dried before analysis.

TABLE 16

| | Modification obtained by XRPD | | |
|---|---|---|---|
| Solvent | 2 hours | 12 hours | 24 hours |
| Methanol | / | $S_B$ | $S_B$ |
| Methanol/water (99.5/0.5) | / | $S_B$ | $S_B$ |
| Methanol/water (99.3/0.7) | / | $S_B$ | $S_B$ |
| Methanol/water (99.0/1.0) | / | $S_B$ | $S_B + S_C$ |
| Methanol/water (95.0/5) | / | $S_C$ | $S_C$ |

/ = no crystallization observed

EXAMPLE 28

About 100 mg of form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide is dissolved in about 2 mL of a solvent listed below at 60° C. The solution is cooled down to 45° C. The suspension is centrifuged but the solid is not dried before analysis.

TABLE 17

| | Modification obtained by XRPD | | |
|---|---|---|---|
| Solvent | 2 hours | 12 hours | 24 hours |
| Methanol | / | / | $S_B$ |
| Methanol/water (99.5/0.5) | / | / | $S_B + S_C$ |
| Methanol/water (99.3/0.7) | / | / | $S_B$ partial + $S_C$ |
| Methanol/water (99.0/1.0) | / | / | $S_C$ |
| Methanol/water (95.0/5) | / | / | $S_C$ |

/ = no crystallization observed

EXAMPLE 29

The solubility of form A, form B and form C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide was determined by gravimetric techniques at different temperature in various solvents. The results are set forth below in Tables 18-20.

TABLE 18

Solubility at Different Temperatures after 24 Hours

| | | Form A | | Form B | | Form C | |
|---|---|---|---|---|---|---|---|
| T (° C.) | Solvent | Solubility (mg/mL) | XRPD | Solubility (mg/mL) | XRPD | Solubility (mg/mL) | XRPD |
| 25 | Water | 0.35 | A | 1.28 | B | 1.47 | C + A |
| | 0.1 N HCl | 1.32 | A | 2.36 | B | 2.35 | A |
| | 0.01 N HCl | 0.43 | A | 0.69 | B | 1.37 | A |
| | 0.001 N HCl | 0.92 | A | 0.70 | B | 1.29 | C + A |
| | 0.0001 N HCl | 0.45 | A | 0.47 | B | 1.67 | C + A |
| | Methanol | 13.79 | B | 14.37 | B | 18.20 | B |
| 50 | Water | 1.03 | A | 1.40 | B | 1.31 | A |
| | 0.1 N HCl | 2.46 | A | 6.62 | B + A | 8.30 | A+ |
| | 0.01 N HCl | 0.85 | A | 1.44 | B | 1.69 | A |
| | 0.001 N HCl | 0.79 | A | 1.34 | B | 6.72 | A |
| | 0.0001 N HCl | 0.90 | A | 1.32 | B | 3.51 | A |
| | Methanol | 52.47 | C + B | 52.11 | B | 55.26 | B |

TABLE 19

Solubility at Different Temperatures in Methanol/Water (99.5/0.5) v/v

| | | Form A | | Form B | | Form C | |
|---|---|---|---|---|---|---|---|
| T (° C.) | Time | Solubility (mg/mL) | XRPD | Solubility (mg/mL) | XRPD | Solubility (mg/mL) | XRPD |
| −10 | 10 minutes | 24.01 | A | 7.62 | B | 11.91 | C |
| | 1 hour | 26.37 | A | 5.63 | B | 7.99 | C |
| | 24 hours | 4.96 | B | 4.00 | B | 6.12 | A (B when duplicated) |
| 20 | 10 minutes | 33.69 | A + B | 12.90 | B | 24.34 | C |
| | 1 hour | 19.30 | A + B | 13.78 | B | 17.70 | C + B |
| | 24 hours | 12.19 | B | 12.21 | B | 12.09 | B |
| 45 | 10 minutes | 52.23 | A + B | 33.29 | B | 39.86 | C |
| | 1 hour | 62.49 | C + B | 39.39 | B | 46.15 | C |
| | 24 hours | 41.86 | C + B | 40.40 | B | 45.59 | C + B |

TABLE 20

Solubility at Different Temperatures in Methanol/Water (95/5) v/v

| T (° C.) | Time | Form A Solubility (mg/ml) | XRPD | Form B Solubility (mg/ml) | XRPD | Form C Solubility (mg/ml) | XRPD |
|---|---|---|---|---|---|---|---|
| −10 | 10 minutes | 12.33 | A | 9.42 | B | 9.73 | C |
|  | 1 hour | 14.40 | A | 6.65 | B | 7.74 | C |
|  | 24 hours | 4.74 | B | 4.85 | B | 11.00 | C |
| 20 | 10 minutes | 25.69 | A | 13.64 | B | 18.88 | C |
|  | 1 hour | 28.18 | A | 13.43 | B | 13.03 | C |
|  | 24 hours | 13.07 | B | 13.01 | B | 11.76 | C |
| 45 | 10 minutes | 46.08 | A | 34.49 | B | 37.68 | C |
|  | 1 hour | 61.15 | A + B + C | 38.18 | B | 31.15 | C |
|  | 24 hours | 36.80 | C | 41.70 | B | 32.26 | C |

As can be seen from the tables above, the solubility at 25° C. and 50° C. after 24 hours of 4-methyl-N-[3-(4-methyl-imidazol-1-yl)-5-trifluoromethyl-phenyl]-3-(4-pyridin-3-yl-pyrimidin-2-ylamino)-benzamide hydrochloride in aqueous media such as water, pH 1, 2, 3 and 4 (dilution with HCl) follows the tendency: form C>form B>form A. In the presence of a large amount of methanol, then the solubility after 10 minutes follows the tendency: form A>form C>form B.

EXAMPLE 30

Form A of the free base of 4-methyl-N-[3-(4-methyl-imidazol-1-yl)-5-trifluoromethyl-phenyl]-3-(4-pyridin-3-yl-pyrimidin-2-ylamino)-benzamide is made according to the following scheme:

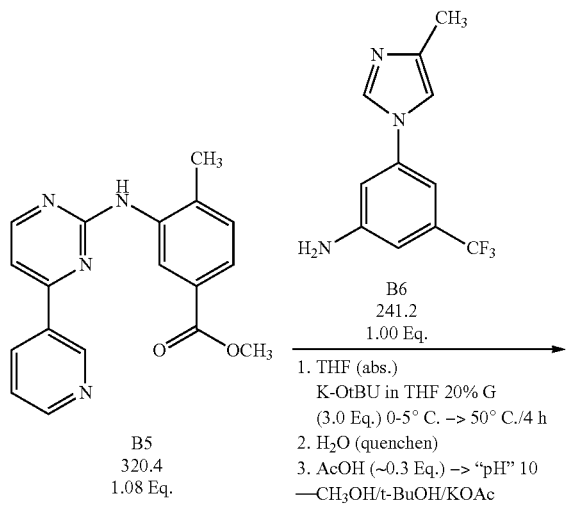

14.5 g (60.0 mmol) of B6 and 20.8 g (64.8 mmol) of B5 are dissolved in 120 mL tetrahydrofuran absolute at room temperature under inert and water-free conditions. The suspension is cooled to IT 0-5° C. and 101.0 g (180 mmol) of potassium tert-butoxide solution 20% in tetrahydrofuran were added within 1 hour, maintaining the internal temperature at 0-5° C. The reaction mixture is heated gradually to IT 50° C. within 1 hour and then stirred at this temperature for another 1 hour. The reaction mixture (yellow suspension) is quenched at IT 50° C. by the addition of 50 mL of water. Stirring is stopped, and the two phase system is let to separate. The aqueous (lower) phase is removed. Seeding crystals (0.2 g) of form A are added to the remaining organic phase, and the thin suspension is stirred for 1 hour at 50° C. during which time crystallization is initiated. Approximately 1.0 mL of acetic acid is added to the organic phase until a pH of ~10 is reached. Solvent (260 mL) is distilled off at 80-100° C. (external temperature) under normal pressure, and simultaneously 260 mL ethanol 94% is added keeping the volume constant, i.e., solvent exchange from tetrahydrofuran to ethanol. The suspension is cooled to IT 0-5° C. within 1 hour, and agitation is continued for another 1 hour. Form A of the free base of 4-methyl-N-[3-(4-methyl-imidazol-1-yl)-5-trifluoromethyl-phenyl]-3-(4-pyridin-3-yl-pyrimidin-2-ylamino)-benzamide (crystalline solid) is collected by filtration and washed with 150 mL of cold ethanol 94%. The product is then dried at 50° C. in vacuo.

EXAMPLE 31

Form B of the free base of 4-methyl-N-[3-(4-methyl-imidazol-1-yl)-5-trifluoromethyl-phenyl]-3-(4-pyridin-3-yl-pyrimidin-2-ylamino)-benzamide is made according to the following scheme:

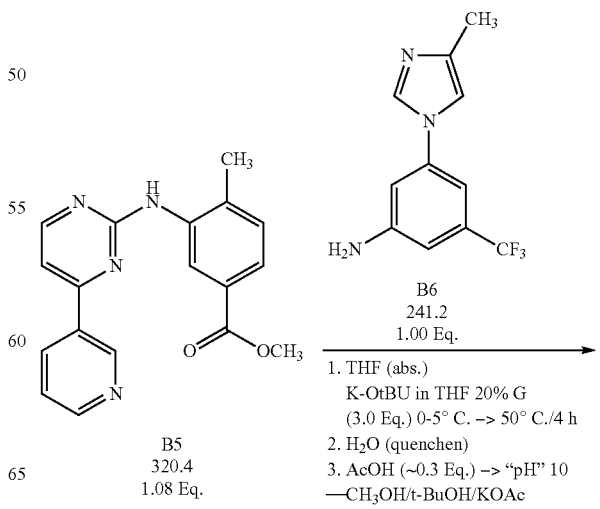

-continued

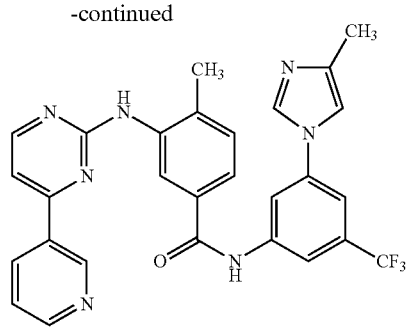

B7
529.5

14.5 g (60.0 mmol) of B6 and 20.8 g (64.8 mmol) of B5 are dissolved in 120 mL tetrahydrofuran absolute at room temperature under inert and water-free conditions. The suspension is cooled to IT 0-5° C. and 101.0 g (180 mmol) of potassium tert-butoxide solution 20% in tetrahydrofuran were added within 1 hour, maintaining the internal temperature at 0-5° C. The reaction mixture is heated gradually to IT 50° C. within 1 hour and then stirred at this temperature for another 1 hour. The reaction mixture (yellow suspension) is quenched at IT 50° C. by the addition of 50 mL of water. Stirring is stopped, and the two phase system is let to separate. The aqueous (lower) phase is removed. Approximately 1.0 mL of acetic acid is added to the organic phase until a pH of ~10 is reached. Seeding crystals (0.2 g) of form B are added to the organic solution. Solvent (260 mL) is distilled off at 80-100° C. (external temperature) under normal pressure, and simultaneously 260 mL ethanol 94% is added keeping the volume constant, i.e., solvent exchange from tetrahydrofuran to ethanol. The suspension is cooled to IT 0-5° C. within 1 hour, and agitation is continued for another 1 hour. Form B of the free base of 4-methyl-N-[3-(4-methyl-imidazol-1-yl)-5-trifluoromethyl-phenyl]-3-(4-pyridin-3-yl-pyrimidin-2-ylamino)-benzamide (crystalline solid) is collected by filtration and washed with 150 mL of cold ethanol 94%. The product is then dried at 50° C. in vacuo.

Chemical, Physicochemical and Morphic Characteristics

The chemical, physicochemical and morphic characteristics of both 4-methyl-N-[3-(4-methyl-imidazol-1-yl)-5-trifluoromethyl-phenyl]-3-(4-pyridin-3-yl-pyrimidin-2-ylamino)-benzamide free base (form B) and 4-methyl-N-[3-(4-methyl-imidazol-1-yl)-5-trifluoromethyl-phenyl]-3-(4-pyridin-3-yl-pyrimidin-2-ylamino)-benzamide monohydrate hydrochloride salt (form B) were evaluated as described below.

Determination of Approximate Solubility: A weighted amount (20-50 mg) of sample was charged into 2 mL of the solvent. The obtained slurry was allowed to equilibrate for 24 hours at room temperature and then filtered. The concentration of DS in saturated filtrate was measured by either UV or HPLC.

Intrinsic Dissolution Rate (IDR): Dissolution rate measurements were performed at 37° C. using the rotating disk method (VanKell Instrument). A single rotation speed of 200 rpm was used. For IDR in 0.1 N HCl, an 800 mL volume, and for IDR in water, a 200 mL volume were used. The solution was continuously pumped through a UV measuring cell and recycled to the dissolution vessel.

TABLE 21

Chemical and Physicochemical Characteristics

| Parameter | Salt form | | | |
|---|---|---|---|---|
| | Free base form B | | Hydrochloride monohydrate (form B) | |
| Elementary analysis | Calculated | Found | Calculated | Found |
| % C | 63.46 | 63.58 | 57.58 | 57.66 |
| % H | 4.15 | 3.97 | 4.29 | 4.25 |
| % F | 10.76 | 10.22 | 9.77 | 9.83 |
| % N | 18.51 | 18.57 | 16.80 | 16.58 |
| % O | 3.02 | 3.56 | 5.48 | 5.68 |
| % Cl | N/A | N/A | 6.08 | 6.00 |
| DSC purity (mol %) (10° C./minute) | 98.65 | | N/A due to decomposition prior to melting | |
| HPLC purity (area %) | 100.00 | | 100.00 | |
| DSC melting point (° C.) (10° C./minute) | 249.0 | | N/A due to decomposition prior to melting | |
| Melting enthalpy (J/g) | 153.9 | | N/A due to decomposition prior to melting | |
| pH of 1% solution or suspension in water | 7.99 | | 2.53 | |
| Solubility (approximately at 25° C., mg/mL) | | | | |
| 0.1N HCl | 0.60 | | 0.94 | |
| 0.01N HCl | 0.0014 | | 0.08 | |
| Phosphate buffer, pH 6.8 | 0.0002 | | Below detection | |
| Water | Below detection | | 0.17 | |
| Ethanol | 0.63 | | 3.69 | |
| Isopropanol | 0.33 | | 1.93 | |
| Thermogravimetry (weight loss %) (10° C./minute) | 0.026 (RT to 200° C.) | | 0.91 (RT to 80° C.) | |
| Residual solvents (%) | 0.2 | | 0.0 | |
| Intrinsic dissolution rate (mg min$^{-1}$cm$^{-2}$) | | | | |
| pH 1 (0.1N HCl) | 0.17 | | 0.17 | |
| Water | 0.0013 | | 0.0024 | |

Thermogravimetry studies were undertaken for each of forms A, B and C of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide. The results are shown in Table 22 below.

TABLE 22

| Form | Loss on drying | | Stoichiometry | Interpretation |
|---|---|---|---|---|
| A | 5.69% | 5.69 (200° C.) | 2 (theory 5.9%) | Dihydrate |
| B | 4.02% | 1.00 (30° C.-100° C.) | / | Residual water |
| | | 3.02 (100° C.-220° C.) | 1 (theory 3.1%) | Monohydrate |
| C | 3.50% | 0.51 (30° C.-80° C.) | / | Residual water |
| | | 2.99 (80° C.-220° C.) | 1 (theory 3.1%) | Monohydrate |

The intrinsic dissolution rate was also determined for each of form A, form B, form C and the amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide in various solvents. The measurements were carried out on a VanKel instrument using a Cary 100 photometer. The results are shown in Table 23 below.

TABLE 23

| Dissolution medium | Intrinsic Dissolution Rate value (mg/min/cm$^2$) | | | |
|---|---|---|---|---|
| | Form A | Form B | Form C | Amorphous |
| HCl 0.1N | 0.6778/1.2467 | 0.1003 | 0.2323/0.3213 | 0.2508 |
| HCl 0.01N | 0.0178 | 0.0224 | 0.0247 | / |
| HCl 0.001N | 0.0089 | 0.0045 | 0.0057 | / |
| HCl 0.0001N | 0.0003 | 0.0010 | 0.0004 | / |
| pH 2 (citrate buffer) | 0.0076 | / | 0.0099 | 0.0250 |
| Water | 0.0004 | 0.0001 | 0.000 | / |

Further stability studies were also undertaken for all of form A, form B, form C and the amorphous form of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide. No form transitions were observed for forms A, B and C after storage at various relative humidities; the amorphous form of the hydrochloride salt spontaneously crystallizes to form A. In addition, each of the forms has good chemical stability for 1 month at 50° C., for 1 month at 80° C. and for 1 month at 80° C. and 75% relative humidity, though both form C and the amorphous form showed a mixture with form A under the last condition.

Crystallographic investigations were undertaken for form B and form $S_B$ of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide. Suitable single crystals were obtained by slow solvent evaporation in methanol at room temperature. The results are set forth in Table 24 below.

TABLE 24

| | Form B | Form $S_B$ |
|---|---|---|
| Crystal system | Orthorhombic | Orthorhombic |
| Space group | P 2$_1$2$_1$2$_1$ | P 2$_1$2$_1$2$_1$ |
| a, Å | 7.6316(4) | 7.596(6) |
| b, Å | 15.322(2) | 16.048(9) |
| c, Å | 24.140(3) | 23.73(2) |
| V, Å$^3$ | 2822.6(5) | 2893(4) |
| D$_{calc}$, g cm$^{-3}$ | 1.369 | 1.447 |
| Z | 4 | 4 |
| Radiation, Å | 1.5406 | 1.5406 |
| Θ range, ° | 5.00-60.00 | 3.32-58.92 |
| No. variables refined | 37 | 404 |
| No. reflect. Refined | 511 | 4147 |
| GOF/R$_{Bragg}$ | 3.8 | 1.020 |
| Final R$_1$ [1 > 2σ(1)]/R$_P$ | 0.1168 | 0.0572 |
| Final wR$_1$ [1 > 2σ(1)]/R$_{WP}$ | 0.1368 | 0.1147 |

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A crystalline form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as a monohydrate, characterized by an x-ray powder diffraction pattern having at least one maxima selected from about 7.2°, 9.2°, 11.4°, 12.0°, 12.3°, 14.6°, 14.8°, 15.7°, 17.6°, 19.2°, 19.5,° 20.5°, 22.0°, 23.4°, 23.9°, 25.0°, 25.5°, 25.9°, 27.0° (2θ degrees) as shown in FIG. 8.

2. The crystalline form of claim 1, characterized by an x-ray powder diffraction pattern having maxima at about 7.2°, 9.2°, 11.4°, 12.0°, 12.3°, 14.6°, 14.8°, 15.7°, 17.6°, 19.2°, 19.5,° 20.5°, 22.0°, 23.4°, 23.9°, 25.0°, 25.5°, 25.9°, 27.0° (2θ degrees).

3. A pharmaceutical composition comprising:
   (a) a therapeutically effective amount of crystalline form B of the hydrochloride salt of 4-methyl-N-[3-(4-methyl-imidazol-1-yl)-5-trifluoromethyl-phenyl]-3-(4-pyridin-3-yl -pyrimidin-2-ylamino)-benzamide as a monohydrate according to claim 1; and
   (b) at least one pharmaceutically acceptable carrier, diluent or excipient.

4. A method of treating chronic myelogenous leukemia comprising the step of administering to a subject in need thereof, a therapeutically effective amount of crystalline form B of the hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide as a monohydrate according to claim 1.

5. A crystalline form B' of the anhydrous hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide, characterized by an x-ray powder diffraction pattern having at least one maxima selected from about 7.2°, 9.2°, 11.5°, 12.0°, 13.9°, 14.3°, 15.4°, 17.6°, 18.6°, 20.3°, 21.7°, 22.5°, 23.2°, 24.7°, 24.9°, 25.2°, 26.0°, 26.6°, 27.5°, 28.2°, 29.2° and 30.0° (2θ degrees) as shown in FIG. 9.

6. The crystalline form of claim 5, characterized by an x-ray powder diffraction pattern having maxima at about 7.2°, 9.2°, 11.5°, 12.0°, 13.9°, 14.3°, 15.4°, 17.6°, 18.6°, 20.3°, 21.7°, 22.5°, 23.2°, 24.7°, 24.9°, 25.2°, 26.0°, 26.6°, 27.5°, 28.2°, 29.2° and 30.0° (2θ degrees).

7. A pharmaceutical composition comprising:
   (a) a therapeutically effective amount of crystalline form B' of the anhydrous hydrochloride salt of 4-methyl-N-[3-(4-methyl-imidazol-1-yl)-5-trifluoromethyl-phenyl]-3-(4-pyridin-3-yl -pyrimidin-2-ylamino)-benzamide according to claim 5; and
   (b) at least one pharmaceutically acceptable carrier, diluent or excipient.

8. A method of treating chronic myelogenous leukemia comprising the step of administering to a subject in need thereof, a therapeutically effective amount of crystalline form B' of the anhydrous hydrochloride salt of 4-methyl-N-[3-(4-methyl-imidazol-1-yl)-5-trifluoromethyl-phenyl]-3-(4-pyridin-3-yl-pyrimidin-2-ylamino)-benzamide according to claim 5.

* * * * *